(12) United States Patent
Sherman

(10) Patent No.: US 7,269,454 B2
(45) Date of Patent: Sep. 11, 2007

(54) METHODS AND DEVICES TO GUIDE THERAPY FOR VENTRICULAR FIBRILLATION BASED ON WAVEFORM ANALYSIS AND SURVIVAL BENEFIT ANALYSIS

(76) Inventor: Lawrence Duane Sherman, 18544 NE. 19th Pl., Bellevue, WA (US) 98008

( * ) Notice: Subject to any disclaimer, the term of this patent is extended or adjusted under 35 U.S.C. 154(b) by 329 days.

(21) Appl. No.: 11/020,315

(22) Filed: Dec. 27, 2004

(65) Prior Publication Data

US 2005/0245974 A1    Nov. 3, 2005

Related U.S. Application Data

(60) Provisional application No. 60/521,465, filed on Apr. 30, 2004.

(51) Int. Cl.
*A61N 1/39* (2006.01)
(52) U.S. Cl. ............................. 600/515; 600/518; 607/5
(58) Field of Classification Search ................ 600/515, 600/518; 607/5
See application file for complete search history.

(56) References Cited

U.S. PATENT DOCUMENTS

| | | | |
|---|---|---|---|
| 5,545,182 A | 8/1996 | Stotts | |
| 5,683,424 A | 11/1997 | Brown | |
| 5,957,856 A | 9/1999 | Weil | |
| 6,171,257 B1 | 1/2001 | Weil | |
| 6,263,238 B1 * | 7/2001 | Brewer et al. ................. | 607/5 |
| 6,438,419 B1 | 8/2002 | Callaway | |
| 6,440,082 B1 * | 8/2002 | Joo et al. .................... | 600/528 |
| 6,539,256 B1 | 3/2003 | KenKnight | |
| 6,650,936 B2 | 11/2003 | Sullivan | |
| 6,671,547 B2 | 12/2003 | Lyster | |
| 6,760,621 B2 | 7/2004 | Walcott | |
| 6,766,195 B1 | 7/2004 | Bornzin | |
| 2004/0230241 A1 * | 11/2004 | Carlson et al. ............... | 607/25 |

OTHER PUBLICATIONS

Watson, James N et al., Improved prediction of defibrillation success for out-of-hospital VF cardiac arrest using wavelet transform methods, Resuscitation 63 (2004) 269-275.

* cited by examiner

*Primary Examiner*—Carl Layno
*Assistant Examiner*—Shevon E Johnson

(57) ABSTRACT

A method of determining a state of ventricular fibrillation from a waveform, includes: performing calculations on the Fourier transform of the waveform voltage values by using the quotient of the power in a high frequency band and of the power in a low frequency band; and determining the state of ventricular fibrillation by relating this ratio to the state of ventricular fibrillation. A defibrillation system for use in treatment of ventricular fibrillation includes at least one sensor to measure heart rhythm and at least one applicator to apply a defibrillation shock to a patient. The system further includes at least one processor which is adapted to calculate the ratio and also to obtain user input regarding survival of subgroups and average response times in the user's domain which allows calculation of an estimated maximum overall survival and selection of an optimum threshold for the ratio measure based on this maximum. The system further includes a user interface system in operative connection with the processor to provide information related to the ratio to a user.

23 Claims, 18 Drawing Sheets

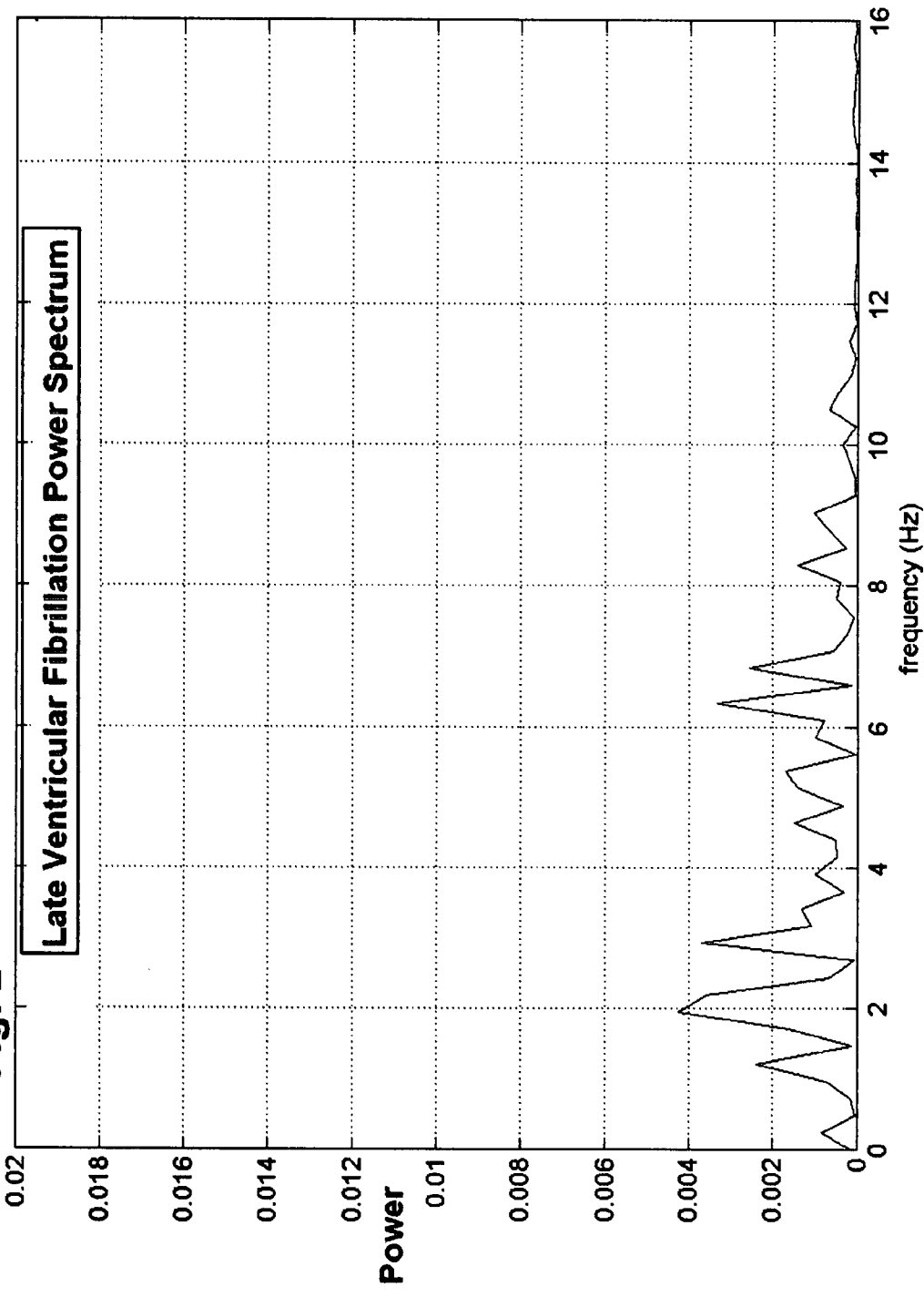

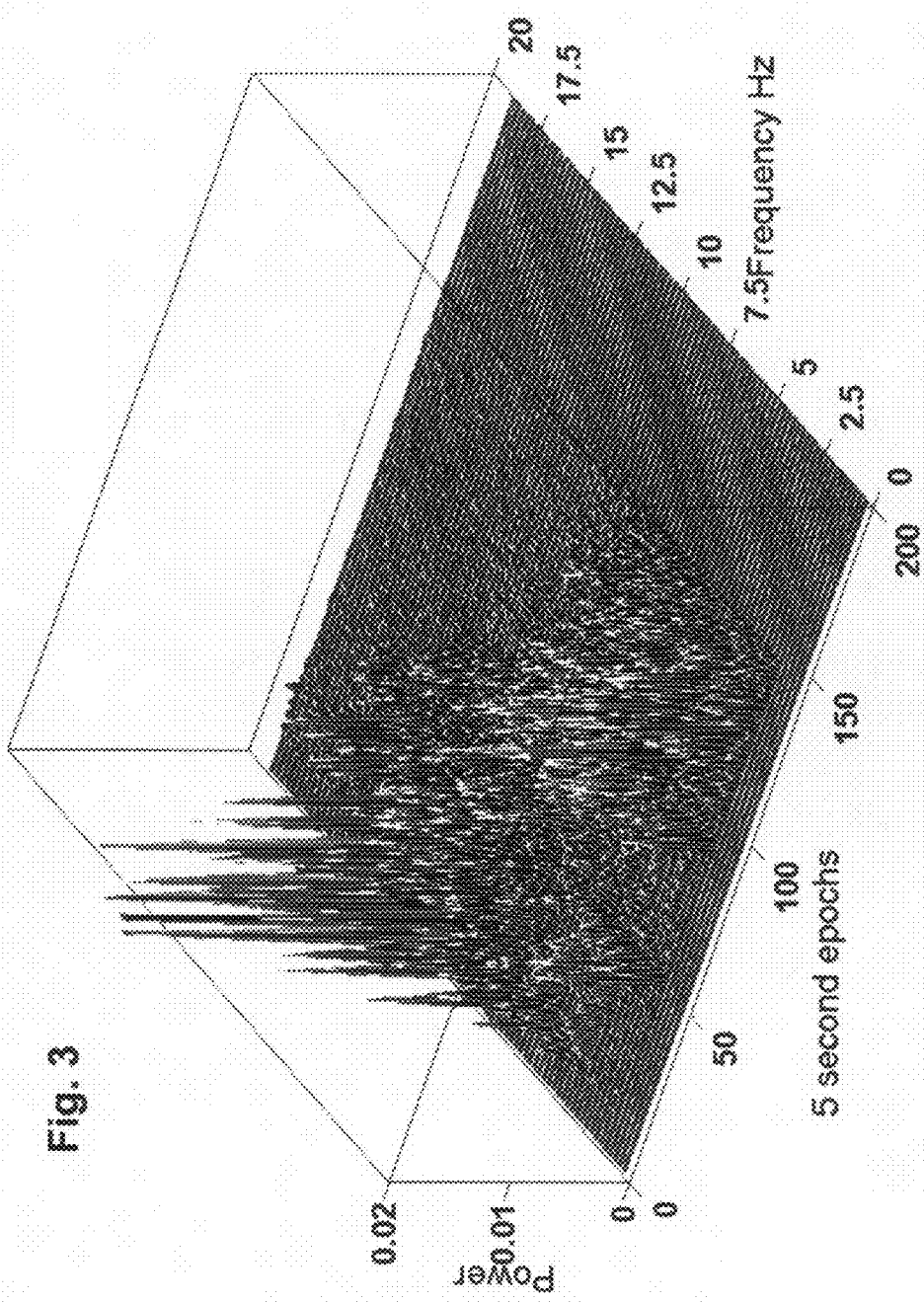

Fig. 4  Survival for Study Groups with VF

| VF Duration | <4 min. Cobb | <5 min. Wik | >4 min. Cobb | >5 min. Wik |
|---|---|---|---|---|
| Immediate Defib | 31% | 29% | 17% | 4% |
| CPR First | 32% | 23% | 27% | 22% |

RESULTING ESTIMATES OF SURVIVAL

| VF Duration | < 5 min. | | | > 5 min. |
|---|---|---|---|---|
| Immediate Defib | 30% | | | 10% |
| CPR First | 27% | | | 25% |

Prior Art  Fig. 12

METHODS AND DEVICES TO GUIDE THERAPY FOR VENTRICULAR FIBRILLATION BASED ON WAVEFORM ANALYSIS AND SURVIVAL BENEFIT ANALYSIS

CROSS-REFERENCE TO RELATED APPLICATIONS

This application uses the Logarithm of the Absolute Correlations for which I made Provisional Patent Application Ser. No. 60/521,465, filed Apr. 30, 2004,

FEDERALLY SPONSORED RESEARCH

Not Applicable

SEQUENCE LISTING OR PROGRAM

The computer code involved in the LR calculations is incorporated into application at end of DETAILED DESCRIPTION OF INVENTION section of this application.

BACKGROUND OF THE INVENTION

1. Field of the Invention

The present invention is directed to methods, systems and devices for the characterization of cardiac rhythms and, particularly, characterization of ventricular fibrillation and to methods, systems and devices to be used in the treatment of ventricular fibrillation based upon the characterization of ventricular fibrillation.

References set forth herein may facilitate understanding of the present invention or the background of the present invention. Inclusion of a reference herein is not intended to and does not constitute an admission that the reference is available as prior art with respect to the present invention.

2. Prior Art

Ventricular Fibrillation (VF) is the initial rhythm in 40% of cardiac arrests thereby accounting for approximately 140,000 such events yearly in the U.S. alone. In ventricular fibrillation of short duration, immediate defibrillation is universally accepted as the most effective therapy. This is reflected in the current recommendations for 3 initial shocks when VF is the presenting rhythm. See, for example, American Heart Association in Collaboration with the International Liaison Committee on Resuscitation, "Guidelines 2000 for Cardiopulmonary Resuscitation and Emergency Cardiovascular Care: an international consensus on science," Circulation, 102(8) (Suppl.I):I-136-57 2000, and American Heart Association in Collaboration with the International Liaison Committee on Resuscitation, "International Guidelines 2000 for CPR and ECC: a consensus on science," Resuscitation, 46(1-3):1-447 2000. When prolonged VF is present, as defined by VF of over 4 minutes duration, there is compelling evidence that CPR prior to defibrillation improves survival. See, Cobb LA, Fahrenbruch C, Walsh T, Copass M, Olsufka M, Breskin M, Hallstrom A. Influence of cardiopulmonary resuscitation prior to defibrillation in patients with out-of-hospital ventricular fibrillation. *JAMA* 1999; 281 (13): 1182-8; and Wik L, Hansen T B, Fylling F, Steen T, Vaagnes P, Auestad B H, Steen P A. Delaying defibrillation to give basic cardiopulmonary resuscitation to patients with out-of-hospital ventricular fibrillation. *JAMA* 2003; 289 (11): 1389-95. In the Seattle study by Cobb et al., patients with ambulance response times of over 4 minutes who received CPR for 90 seconds had an observed survival increase from 17% without CPR to 27% with CPR being given first. In the study by Wik et al. based in the Netherlands, patients with ambulance responses times over 5 minutes who received CPR for 3 minutes prior to defibrillation demonstrated an increased survival from 4% without CPR to 22% with CPR first. Based on these studies, survival from prolonged ventricular fibrillation, defined as VF of over 5 minutes duration could be improved by over 10% if CPR would be provided prior to defibrillation. In order to provide immediate defibrillation to those in the first 5 minutes who have the highest probability of response, while giving those with prolonged VF the benefit of CPR, a quantitative method to estimate VF duration is essential. Since the duration of VF is difficult to determine with accuracy in the field, a reliable method based on the ECG waveform would be very useful.

Waveform analysis has progressed significantly over the past 20 years. Early methods to select patients more likely to respond to defibrillation were based on amplitude and the average (median) frequency of short segments of the signal. See, Weaver W D, Cobb L A, Dennis D, Ray R, Hallstrom A P, Copass M K. Amplitude of ventricular fibrillation waveform and outcome after cardiac arrest. *Ann Intern Med* 1985; 102 (1): 53-5; and Dzwonczyk R, Brown C G, Werman H A. The median frequency of the ECG during ventricular fibrillation: its use in an algorithm for estimating the duration of cardiac arrest. *IEEE Trans Biomed Eng* 1990; 37: 640-6. Proposed strategies have sought to insure that those who have VF of less than 5 minutes duration, or would respond to defibrillation with "return of organized rhythm" (ROOR) or "return of spontaneous circulation" (ROSC), would receive an immediate shock at least 95% percent of the time. Using the 95% "cutpoint" (a term meaning a threshold often used with Receiver Operating Characteristic (ROC) curves) for sensing the "TRUE POSITIVES" (i.e. those with VF duration under 5 minutes or with ROOR/ROSC as a response to immediate defibrillation) as the baseline, the focus was then directed at detecting the highest percentage possible of "TRUE NEGATIVES", that is: those who would not respond to the initial defibrillation attempt and therefore should receive CPR and other therapies to increase survival by the estimated 10-15% as demonstrated in the studies cited above. We note that overall survival may be maximized by lowering the sensitivity for detecting TRUE POSITIVES in order to increase capture of the TRUE NEGATIVES. This will be addressed in detail in the survival benefit analysis portion of this application. While using a 95% cutpoint does not optimize survival, it does serve as a recognized point to be used to compare the various methods of waveform analysis. Using this 95% cutpoint for detecting VF of less than 5 minutes as our comparison point, our data show that amplitude allows only 4%, and median frequency only 51% of prolonged VF to be selected.

Measurement of amplitude has been further refined by considering the fractal dimension of the waveform, a measure termed the scaling exponent (ScE). See, Callaway C W, Sherman L D, Menegazzi J J, Scheatzle M D. Scaling structure of electrocardiographic waveform during prolonged ventricular fibrillation in swine. *Pacing Clin Electrophysiol* 2000; 2: 180-91; and U.S. Pat. No. 6,438,419, the disclosures of which are incorporated herein by reference. The ScE measures the roughness of the waveform quantitatively by analyzing the signal for self-similarity. The pattern of peaks in the waveform is examined at smaller and smaller scales or magnifications. When there are similar patterns at several decreasing scales, a region of "scaling" is identified. This method works well in the laboratory at recording rates of 1000 samples/second and with no filtering. Using the scaling exponent, 20% of TRUE NEGATIVES, defined as VF of over 5 minutes duration, can be identified when the 95% cutpoint is used for comparison. Unfortunately, when applied to data obtained at recording rates of 125 samples/second and with low pass filtering below 60 Hz characteristic of currently used defibrillators, the scaling regions are no longer seen. This observation motivated our search for a method which would quantitatively measure the features of VF related to amplitude but which could be used in current clinical devices. This method is the Logarithm of the Absolute Correlations, or LAC. See, U.S. Patent Provisional Application Ser. No. 60/521,465, filed Apr. 30, 2004, the disclosure of which is incorporated herein by reference.

The frequency spectrum and frequency based measures have also been exploited. These have focused either on Fourier analysis. See Dzwonczyk, R, et al., "The median frequency of the ECG during ventricular fibrillation: its use in an algorithm for estimating the duration of cardiac arrest," *IEEE Trans Biomed Eng*, 37: 6406 1990; Brown, C G and Dzwonszyk, R, "Signal analysis of the human electrocardiogram during ventricular fibrillation: frequency and amplitude parameters as predictors of successful countershock," *Ann Emerg Med*, 27(2): 184-8, 1996; Berg, R A, et al., "Precountershock cardiopulmonary resuscitation improves ventricular fibrillation median frequency and myocardial readiness for successful defibrillation from prolonged ventricular fibrillation: a randomized, controlled swine study," *Ann Emerg Med*,40(6): 563-70, 2002; U.S. Pat. Nos. 5,077,667, 5,957,856 and 6,171,255. Another novel frequency based measure based on chaos theory and "attractor reconstruction" called the "Angular Velocity" (AV) has also been used. See, Sherman L D, Callaway C W, Menegazzi J J. Ventricular fibrillation exhibits dynamical properties and self-similarity. Resuscitation 2000; 47(2): 163-73; and Sherman L D, Flagg A, Callaway C W, Menegazzi J J, Hsieh M. Angular velocity: a new method to improve prediction of ventricular fibrillation duration. Resuscitation 2004; 60: 79-90. In Fourier based methods, the "Median Frequency" is usually employed. The MF is a weighted measure that produces a measure of the 'center of mass' of the frequency spectrum when applied to a short segment of VF. It follows a multiphasic pattern which limits its ability to distinguish appropriate phases of VF.

The AV involves reconstruction of a disc-like structure from identical copies of short segments of the VF waveform that are offset by a fixed number of points called the 'lag'. Since the VF is an irregular wave, the offset copies are out of phase. When each set of 3 points is used as a point in a 3 dimensional plot, the plot is said to be in 3 dimensional "phase space" and a disc shaped structure results. As this disc is formed, the leading edge rotates around a central point. The rate of this rotation was noted to be more rapid in early VF and slower at later time periods. When the number of radians of rotation for each second is averaged, this is a measure termed the Angular Velocity.

The MF and AV follow very similar patterns, although the AV does not rise at later time periods as is seen for the MF. At the 95% cutpoint used for comparison, MF detects 51% and the AV detects 60% of the TRUE NEGATIVES (VF epochs over 5 minutes) demonstrating its improved ability to distinguish these two important phases of VF.

Amplitude and frequency are essentially the only features of the VF waveform that have been correlated with VF duration. Combining two measures of these features (the ScE for amplitude/scaling and the AV for frequency) in a two dimensional model and using a classification line that is based on optimal separation between TRUE POSITIVES at a 95% cutpoint and TRUE NEGATIVES has increased the detection of TRUE NEGATIVES to 65%. See Sherman et al. *Resuscitation*, 2004;60:79-90 cited above. This method cannot be used in current defibrillators because the recording rates of approximately 120 samples/second and filters (<60 Hz) which are present eliminate the scaling region from which the ScE is calculated. This prompted a search for a method which would function well under these conditions. "Correlations" are a mathematical technique used to estimate the similarity of one signal to another. If the correlation between two signals is high, then there is a large amount of similarity between the signals. Self-similarity of a signal with itself can also be examined. This "autocorrelation" measures how the signal is similar to itself at different points along its length. This differs from the scaling exponent which measures similarity at different magnifications of the signal (i.e. along its height). Study of raw autocorrelations of 5 second intervals of VF showed that large autocorrelations are present in early VF and become smaller with the passage of time. These autocorrelations are deviations above and below the zero baseline. The negative amplitudes can be brought above the zero baseline by taking the absolute values of the correlations. This allows the area under the curve to be summed and for this sum to give a positive result. The logarithm of this sum serves as a measure of the "longitudinal" self-similarity of the waveform. This is termed the "Logarithm of the Absolute Correlations", or LAC. The formula for the LAC being:

$$LAC = Log_{10}(\Sigma_k(|\Sigma_i(X(i) \cdot X(i+N))|)); \{k \text{ from } 1 \text{ to } N, i \text{ from } 1 \text{ to } n-N\}.$$

With a suitable mathematical transformation depending on recording rates, the LAC may be converted to values that closely match the ScE in magnitude. This transformation is called the "LACadjusted". This feature indicates that the self-similarity measured by the fractal dimension (ScE) in the sense of magnification can be closely approximated by the self-similarity measured by the LAC in the longitudinal sense. Of course, for VF they can only be compared at high sampling rates because the ScE does not produce useful information at sampling rates below 250 Hz or when the signal is filtered below about 125 Hz.

While this historical review demonstrates that progress has been made in developing methods for determining the duration of ventricular fibrillation and likelihood of successful defibrillation, it remains desirable to develop improved devices and methods for determining the duration of ventricular fibrillation as well as improved treatment devices, systems, methods and protocols for treatment of ventricular fibrillation based on these. We therefore endeavored to improve the frequency based measures for analyzing VF as follows.

OBJECTS AND ADVANTAGES

Accordingly, several objects and advantages of the present invention are:
(a) to provide a method to measure a characteristic or characteristics of the ventricular fibrillation waveform which is associated with a state or phase of ventricular fibrillation which is based on principles that are distinct from the prior art, and provide for distinct and definite improvements in the ability to separate the phases or states of ventricular fibrillation and therefore to provide information not present in measures represented by the prior art.

(b) to provide a measure of a characteristic or characteristics of the ventricular fibrillation waveform which can be performed on waveform data obtained at sampling rates below 125 samples/second and therefore can be obtained from currently available clinically utilized defibrillators and monitoring devices.

(c) to provide a measure of a characteristic or characteristics of the ventricular fibrillation waveform which can be performed on waveform data which has been filtered with low pass filters that leave only frequencies below 60 hertz and therefore can be obtained from currently available clinically utilized defibrillators and monitoring devices.

(d) to provide a method to optimize survival from ventricular fibrillation by allowing several parameters to be input by a user for an algorithm employing one or more measures of characteristics of ventricular fibrillation which then would indicate projected survival statistics based on the parameters and the measure or measures so that the value of the measure or measures to be used to guide therapy can be set at an optimum value.

Still further objects and advantages will become apparent from a consideration of the ensuing descriptions and drawings.

SUMMARY OF THE INVENTION

In general, the present invention provides a new quantitative measure of the heart rhythm waveform, and particularly, the ventricular fibrillation waveform, related to the quotient of the summed power in two bands of the frequency power spectrum of the ECG waveform as derived from Fourier transformation of the ECG waveform. The quotient of a summation of a high frequency power band and of the summation of the power in a low frequency power band can be calculated from a short interval of a ventricular fibrillation waveform. In studies of the present invention 5 second intervals of waveform were analyzed in less than one second.

Fourier analysis methods involve transforming the time series of data points into the various frequencies of sine and cosine waves which constitute it. The Fourier transform produces a series of amplitudes for each frequency which indicate the proportion or amplitude of that particular frequency of sine or cosine wave which is present in the original signal. It is then possible to recreate the original signal from the frequencies by combining pure sine or cosine waves of each frequency at the amplitude for that frequency as indicated by the transform. When these individual waves are combined in additive fashion, the original signal is seen to have been recreated. The power in the signal at each frequency is defined to be the product of the complex number representing the amplitude of that frequency as produced by the Fourier transform times its complex conjugate. Then, the series of such values representing the power at each frequency present in the transformed signal is called the power spectrum.

The Life Ratio (LR) is based on taking the discrete Fourier transform of a 5 second segment of VF and then calculating its power spectrum by multiplying the complex value at each frequency by its complex conjugate to obtain the power at that frequency. The resulting list of powers in frequencies 3 Hz thru 5 Hz inclusive is then summed to form the lower frequency band and the powers in frequencies 8 Hz thru 24 Hz inclusive are summed to form the high frequency band. The "Life Ratio" (LR) was then formed as the quotient of the high frequency band divided by the low frequency band. The LR may then be used as an estimate of the likelihood of ventricular fibrillation being successfully terminated by an electric shock or as an estimate of duration of VF or as an estimate of probability of survival, etc.

In one aspect, the present invention is a method of determining or characterizing a state of the myocardium. In particular it determines or characterizes a state of ventricular fibrillation of the myocardium, including: measuring the rhythm of the heart during ventricular fibrillation for a period of time; calculating the discrete Fourier transform from the series of voltage values that make up the this measured heart rhythm; summing the power at each frequency for two frequency bands, a low frequency band (for instance from 3 Hz thru 5 Hz) and a high frequency band (for instance from 8 Hz thru 24 Hz); determining a first value related to the high and low frequency bands by taking the quotient of the high frequency power band sum and the low frequency power band sum; and determining the state of ventricular fibrillation by relating the first value to the state of ventricular fibrillation.

The first value may, for example be the quotient of the high frequency power bands described above. It may also be a quotient of two frequency bands with different ranges. For example, the low frequency band could be from 3 Hz to 10 Hz inclusive and the high frequency band from 7 Hz to 24 Hz inclusive. As an example, these ranges may be varied for particular embodiments to produce the highest degree of separation between the groups of patients demonstrating the desired response to a defibrillating electric shock or some effective alternative therapy.

The method can further include determining a second value related to the logarithm of the absolute correlations (LAC) of the ventricular fibrillation heart rhythm for a period of time. In this embodiment, the step determining the state of fibrillation includes the step of relating at least one of the first value and the second value to the state of fibrillation. The first value and the second value are preferably both related to the state of fibrillation.

The ECG waveform output used in calculating the LR and LAC may be filtered and may be obtained at sampling rates which are routinely used in currently available instruments. In several studies of the present invention, sampling rates of 125 samples/second and low pass filtering to eliminate frequencies above 62.5 Hz did not significantly affect the LR or LAC values.

In one embodiment, the determined state of the ventricular fibrillation is associated with a probability of success of a mode of treatment of ventricular fibrillation. The mode of treatment can, for example, be a defibrillation shock. The determination of the probability of success of a defibrillation shock can, for example, be related to both the LR and the LAC. The measured values (or one or more values derived there from) can, for example, be compared to stored or historical values of the variables or to the output of one or more values derived from such values. Values other than the first value and/or second value can also be determined. Moreover, the first and/or second values can be measured over multiple periods of time in determining the state of ventricular fibrillation. The measured first and second values may also be used in conjunction with a third value produced by an algorithm employing several parameters specific to the geographic region or location of operation in which the device, system or method is used. These could include, but are not limited to, the percentage of instances for which the device, system or method is applied to patients in VF cardiac arrest in the time period less than 5 minutes (or some other appropriate time interval) from onset, the percentage of survival for patients when electric shock is given as the initial therapy for VF when VF duration is less than 5 minutes, the percentage of survival when cardiopulmonary resuscitation (CPR) is provided for 3 minutes (or some other appropriate time interval) prior to shock in patients with VF in whom the VF is of less than 5 minutes duration, the percentage of survival for patients when electric shock is given as the first therapy for VF cardiac arrest when the VF duration is over 5 minutes in duration, and the percentage of survival when cardiopulmonary resuscitation is provided for 3 minutes (or some other appropriate time interval) prior to shock in patients with VF when the VF duration is over 5 minutes. This third value derived from the algorithm with these or similar user specific variables can then be used to determine an optimized or maximum probability of survival or of other success of a mode of treatment.

In another embodiment, the invention provides a method of determining a treatment for a patient experiencing ventricular fibrillation, including: measuring the rhythm of the heart during ventricular fibrillation for a period of time; calculating a LR from the voltage values in the measured ventricular fibrillation heart rhythm; determining the first value related to the LR calculated from the rhythm over the period of time; and relating the first value to a treatment of the patient. As described above, the first value can be formed from the discrete Fourier transform of the series of voltage values that make up the measured heart rhythm by summing the powers at each frequency for two frequency bands as follows: one band is a low frequency band (for instance from 3 Hz thru 5 Hz) and the second band is a high frequency band (for instance from 8 Hz thru 24 Hz); the power at each frequency in the band is summed thus producing a high frequency band summation and also a low frequency band summation; the first value is then formed by taking the quotient of the high frequency power band summation and the low frequency power band summation. As also described above, the method can further include determining a second value related to the LAC of the ventricular fibrillation for the period of time. In that embodiment, the step of determining the treatment can include the step of relating at least one of the first value and the second value to the treatment. Once again, the second value can be the LAC or some other measure based on the self-similarity and/or amplitude of the VF waveform segment. In addition, the measured values may also be used in conjunction with a third value derived from an algorithm employing several parameters specific to the geographic region or location of operation in which the device, system or method is used. These could include, but are not limited to, the percentage of the time for which the device, system or method is applied to patients in VF cardiac arrest in the time period less than 5 minutes (or some other appropriate time interval) from onset, the percentage of survival for patients when electric shock is given as the initial therapy for VF when the VF duration is less than 5 minutes, the percentage of survival when cardiopulmonary resuscitation is provided for 3 minutes (or some other appropriate time interval) prior to shock in patients with VF when VF duration is less than 5 minutes from onset, the percentage of survival for patients when electric shock is given as the initial therapy for VF cardiac arrest when VF duration is over 5 minutes, and the percentage of survival when cardiopulmonary resuscitation is provided for 3 minutes (or some other appropriate time interval) prior to shock in patients with VF when VF duration is over 5 minutes from onset. This third value derived from the algorithm with user specific variables could then be used to determine an optimized or maximum probability of survival based and a mode of treatment.

In a further aspect, the present invention provides a system for providing an indication of a state of ventricular fibrillation. The system includes at least one sensor to measure the heart rhythm and at least one processor in communication with the sensor. The processor is adapted to calculate the LR for a period of time and to determine a first value related to the LR for the period of time. The system further includes a user interface system in operative connection with the processor. The user interface system is adapted to determine information related to the first value, for example, over multiple periods of time. The processor can be further adapted to determine a second value related to the LAC of the ventricular fibrillation for the period of time. In this embodiment the user interface system is adapted to provide information related to at least one of the first value and the second value.

In another aspect, the present invention provides a defibrillation system for use in treatment of ventricular fibrillation. The system includes at least one sensor to measure heart rhythm and at least one applicator to apply a defibrillation pulse to a patient (either human or another member of the animal kingdom). The system further includes at least one processor in communication with the sensor and the applicator. The processor is adapted to calculate the LR over a period of time and to determine a first value related to this calculation over the period of time. The system further includes a user interface system in operative connection with the processor to provide information related to the LR to a user. The processor can further be adapted to determine a second value related to the LAC (or other measure of the self-similarity or amplitude) of the ventricular fibrillation waveform for the period of time. In that embodiment, the user interface provides information related to at least one of the first values and the second value. In addition, the processor may be adapted to utilize the measured values in conjunction with a third value derived from an algorithm employing several parameters specific to the geographic region or location of operation in which the defibrillation system is used. These could include, but are not limited to, the percentage of the time for which the system is applied to patients in VF cardiac arrest in the time period less than 5 minutes (or some other appropriate time interval) from onset, the percentage of survival for patients when electric shock is given as the first therapy for VF when VF duration is less than 5 minutes from onset, the percentage of survival when cardiopulmonary resuscitation is provided for 3 minutes (or some other appropriate time interval) prior to shock in patients with VF when VF duration is less than 5 minutes from onset, the percentage of survival for patients when electric shock is given as the first therapy for VF cardiac arrest when VF duration is over 5 minutes from onset, and the percentage of survival when cardiopulmonary resuscitation is provided for 3 minutes (or some other appropriate time interval) prior to shock in patients with VF when VF duration is over 5 minutes. This third value derived from the algorithm with user specific variables could then be used to determine an optimized or maximum probability of survival based on a particular cutoff or threshold value of the LR which would be used as part of the defibrillation system.

In another aspect, the present invention provides a method of creating a relation to characterize ventricular fibrillation including: measuring heart rhythm during ventricular fibrillation for an epoch comprising a period of time for a number of unique epochs; calculating the LR of the measured ventricular fibrillation heart rhythm for each epoch; and determining a first value related to the LR for each epoch. Preferably, the unique epochs are sequential epochs. The unique epochs can, for example, be sequential epochs of approximately 5 seconds.

In still a further aspect, the present invention provides a method of determining a state of a heart rhythm waveform, including: measuring the rhythm of the heart for a period of time; calculating the LR for the period of time; determining a first value related to the LR for the period of time; and determining the state of the heart rhythm waveform by relating the first value to the state of the heart rhythm waveform.

The LR of the ventricular fibrillation waveform varies in a predictable manner over time during ventricular fibrillation and quickly provides a characterization of the ventricular fibrillation waveform that can be related to a "character", "phase", or "state" of ventricular fibrillation. In that regard, ventricular fibrillation appears to exhibit different states which can be associated with different preferred treatment protocols. Such states of ventricular fibrillation can be related to the duration of ventricular fibrillation as untreated ventricular fibrillation appears to pass through various states throughout its duration. For example, the likelihood of successful defibrillation is determined, in significant part, by the duration of ventricular fibrillation, and a measure of ventricular fibrillation duration can serve as a way of estimating the likelihood of shock success. For this purpose, shock success can be defined as the restoration of a perfusing or organized cardiac electrical rhythm, or as the suppression of ventricular fibrillation, within a short period of time following the application of the defibrillation shock (usually within approximately a minute), or as the maximum probability of overall survival benefit to be expected based on the use of an algorithm combining several parameters specific for the user of the device or method which can be input by the user as described above. Duration of ventricular fibrillation is not the only determinant of shock success, however. If, for example, cardiopulmonary resuscitation or CPR is applied for a period of time during ventricular fibrillation, the likelihood of shock success can be greater than if the patient did not receive CPR. Moreover, if ventricular fibrillation is triggered by a progressive ischemic event rather than a sudden electrical event, such ventricular fibrillation is more difficult to shock successfully for the same duration of ventricular fibrillation. The inventor has discovered that certain values related to (or a measure of) the LR, particularly when used in conjunction with a value related to (or a measure of) the self-similarity and/or amplitude of the ventricular fibrillation waveform (such as the LAC) seem to take any and all of the factors affecting the state of ventricular fibrillation into account, allowing, for example, a prediction of shock success to be made without having to consider such individual factors.

The LR, for example, exhibits a distinct pattern in which there is a high initial value over the first 5 minutes after initiation of ventricular fibrillation and then a linear decrease in value until approximately 9 minutes of VF duration. The LR value then remains relatively stable at a low value. In a study of the present invention, when the LR (which took less than 1 second to calculate) was used in the present invention in conjunction with the LAC to establish that less than 5 minutes of ventricular fibrillation had passed, over 95% of waveforms from this period of VF were identified on the basis of a single 5-second recording of the waveform. Using this sensitivity for detecting VF of under 5 minutes duration, it was possible to select 72% of the waveforms which were from VF of over 5 minutes duration. The LR is not altered by recording conditions present in currently used clinical practice, for example, digital recording of the waveform at a rate of less than 125 samples/second and filtering of the ventricular fibrillation waveform by low pass filters which restrict the signal to less than 62.5 hertz frequencies do not alter the values of the LR significantly. The sensitivity of 95% and the negative predictive value of 72% cited above were in VF recorded at 125 samples/second and low pass filtered to below 62.5 hertz. As the appropriate treatment of ventricular fibrillation is strongly dependent upon the state of ventricular fibrillation (which, in turn, is often related to the duration thereof), and as the devices in current clinical use provide for waveform recordings which are limited to lower sampling rates and are filtered to eliminate higher frequencies, the improved devices and methods of the present invention, which provide an indication of the state of ventricular fibrillation from a short segment of heart rhythm recorded with lower sampling rates and with filters that eliminate higher frequencies, provide a significant improvement in the art.

In another aspect of the invention, the Receiver Operating Characteristic (ROC) curves of the LR allow the selection of a "cutpoint" or threshold for sensitivity in detecting VF of less than 5 minutes duration. Each of these cutpoints is also associated with a separate ability (sensitivity) to detect VF of over 5 minutes duration. When analyzing the effective survival benefit of using an algorithm incorporating the LR (possible along with the LAC) in a device to select treatments for ventricular fibrillation, it becomes clear that various parameters may be adjusted to achieve the highest overall survival benefit. In particular, the selection of the cutpoint may be adjusted to achieve the highest overall survival based on the percentage of cases in a geographic region for which responses by Emergency Medical Systems (EMS) personnel (or other individuals who may perform CPR or provide electric shock to defibrillate a patient in VF) are less than 5 minutes. By adjusting the cutpoint to the appropriate sensitivity along the curve produced by modeling the particular response time for that EMS region, overall survival can be optimized (FIG. 7). The selection of the cutpoint to be used for the LR (possibly in conjunction with the LAC) which will in turn determine the treatment (for instance CPR or electric shock) which will be delivered is envisioned as one important aspect of this invention. The processor described in the above embodiments could be set to use a cutpoint for the LR (and possibly the LAC) based on the model to be described below (or similar model) which would provide for an estimated optimum overall survival based on the percentage of EMS responses (or on the percentage of responses of another specific group which would operate the device) which are less than 5 minutes (or some other time period) and based on survival statistics specific to a given region or locale. In one embodiment of the invention, the operator of a system using the LR (or a related frequency based measure such as median frequency and/or an amplitude based measure such as the LAC) would be able to input the average response time or the percentage of response times under some set limit, for instance 5 minutes, which would allow the processor to set the cutpoint or threshold for providing a defibrillation shock or other therapy. The operator could also input other features of the model used to estimate survival benefit, including but not limited to, percentage survival for those patients shocked initially when VF duration is less than 5 minutes, percentage survival for those patients shocked initially when VF duration is over 5 minutes, percentage survival when CPR is performed first for 3 minutes prior to defibrillation shock when VF duration is less than 5 minutes, and percentage of survival when CPR is first performed when VF duration is over 5 minutes. VF durations other than 5 minutes may be used and CPR durations other than 3 minutes may also be used in this embodiment. In summary, the selection of the cutpoint by the algorithm would optimize the overall survival from ventricular fibrillation by using estimates of survival for various subgroups of those in ventricular fibrillation whose response times are greater than or less than a given interval. The operation of the algorithm to indicate an overall survival probability or to indicate a treatment based on the LR would involve input from a user at some point prior to use of the device to treat a patient.

BRIEF DESCRIPTION OF THE DRAWINGS

Other aspects of the invention and their advantages will be discerned from the following detailed description when read in connection with the accompanying drawings, in which:

FIG. 2 illustrates the location of several peaks in the power spectrum typical of late VF with a broadening of the spectrum and no large peaks but several small peaks below 8 Hz.

FIG. 3 illustrates the high peaks in the higher frequencies of the power spectrum typical of early VF and the subsequent broadening and lowering of the power spectrum at later times with almost total absence of power above 8 Hz at later time periods.

FIG. 4 illustrates the method for estimating survival in the four subgroups used in the survival benefit calculations by averaging the survival percentages from the Wik and Cobb studies that are detailed in the top three rows of the table to produce the estimates of survival for the four subgroups that will be used in survival benefit calculations that are seen in the bottom 3 rows of the table.

DETAILED DESCRIPTION OF THE INVENTION

Figure 1:
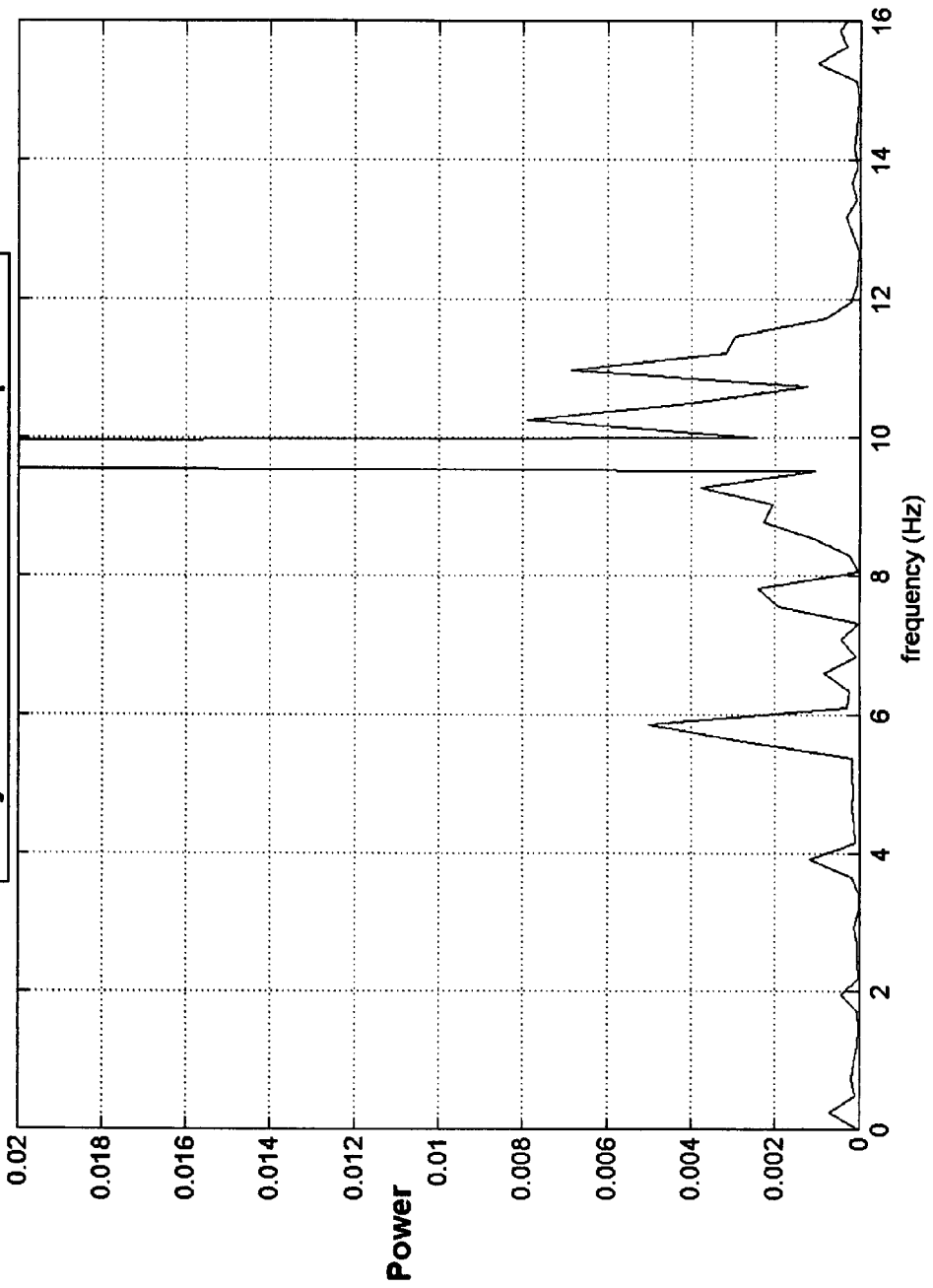
FIG. 1 illustrates the location of several peaks in the power spectrum typical of early VF with one large peak and three small peaks above 8 Hz and two small peaks below 8 Hz.

In studies of the present invention, the ability of the LR (alone or in combination with the LAC) to predict or determine a state, phase or class of ventricular fibrillation as modeled by the duration of ventricular fibrillation was determined. Preliminary study of the frequency power spectrum produced through Fourier analysis of segments of early and late VF demonstrated that there are commonly two or more peaks in the power spectrum of early VF (FIG. 1). In early VF one or more large peaks are often seen above 8 Hz and one or more smaller peaks below 8 Hz. In late or prolonged VF the pattern changes to show several peaks below 8 Hz which are larger in total area than any peaks which may be present above 8 Hz (FIG. 2). In addition, the peaks were prominent with high amplitude in early VF, but tended to broaden and have lower amplitude with almost no power above 8 Hz at later times (FIG. 3). In order to take advantage of these observations, a technique to measure specific "frequency bands" was developed. Extensive exploratory investigation revealed that using a high frequency band from 8 Hz to 24 Hz and a low frequency band from 3 Hz to 5 Hz inclusive would best capture information capable of distinguishing VF of less than 5 minutes duration from that over 5 minutes in duration. Specifically, a discrete Fourier transform of a 5 second interval of data was carried out using a 4096 point transform for 5000 point data sets and a 512 point transform for 625 point data sets. Calculations were performed using MATLAB (Release 12, The Mathworks, Inc.) and by custom software written in C++ using standard Fourier routines from Numerical Recipes in C (Cambridge University Press). In either case the power spectrum was produced by taking the discrete Fourier transform of the 5 second interval of waveform data and multiplying the resulting complex value representing the amplitude at each frequency by its complex conjugate to obtain the power at that frequency. The powers in frequencies 3 Hz thru 5 Hz were then summed to form the lower frequency band summation and the powers in frequencies 8 Hz thru 24 Hz were summed to form the high frequency band summation. The "Life Ratio" (LR) was then defined as the quotient of the high frequency band divided by the low frequency band. The code in C+ and in MATLAB is included at the end of this detailed description which will easily allow these calculations to be performed by one sufficiently skilled in the art.

The ultimate goal for methods used to discriminate early VF from prolonged VF is to develop an algorithm which can be incorporated into a defibrillator or AED for clinical use. This algorithm should guide therapy in a manner resulting in significant increases in survival. Such an algorithm would initially advise immediate defibrillation if VF is found to be less than 5 minutes in duration or alternatively would advise CPR for VF of longer duration. For VF of over 5 minutes duration, an increase in survival of over 10% would be expected. In order to gauge the benefit of such an algorithm, estimates of survival for 4 subgroups involved are used. In the Cobb study, those patients who were defibrillated who had ambulance response times less than 4 minutes had a survival of 31%. See, Cobb L A, Fahrenbruch C, Walsh T, Copass M, Olsuflka M, Breskin M, Hallstrom A. Influence of cardiopulmonary resuscitation prior to defibrillation in patients with out-of-hospital ventricular fibrillation. *JAMA* 1999; 281 (13): 1182-8. In the Wik study from Amsterdam, the survival for those who received immediate defibrillation in the group with response times less than 5 minutes was 29%. See, Wik L, Hansen T B, Fylling F, Steen T, Vaagnes P, Auestad B H, Steen P A, Delaying defibrillation to give basic cardiopulmonary resuscitation to patients with out-of-hospital ventricular fibrillation. *JAMA* 2003; 289 (11): 1389-95. An estimated survival of approximately 30% therefore is made in this study for those with a VF duration of less than 5 minutes who receive immediate defibrillation. Similar estimates are made for the group whose members are given CPR for 3 minutes prior to defibrillation and who have a duration of VF less than 5 minutes, and also for the groups with VF durations over 5 minutes who are either shocked immediately or alternatively are given CPR for 3 minutes prior to defibrillation. The specific data from which these estimates are derived in the two studies and the actual estimates are shown in FIG. 4. In the Cobb study 576 patients had response times less than 4 minutes and 541 were over 4 minutes, while in the Wik study 119 had response times less than 5 minutes and 82 were over 5 minutes. We therefore estimate that 59% of patients would have response times of less than 5 minutes in a general population for the purposes of survival benefit estimate calculations that are directly related to this study.

Figure 7:
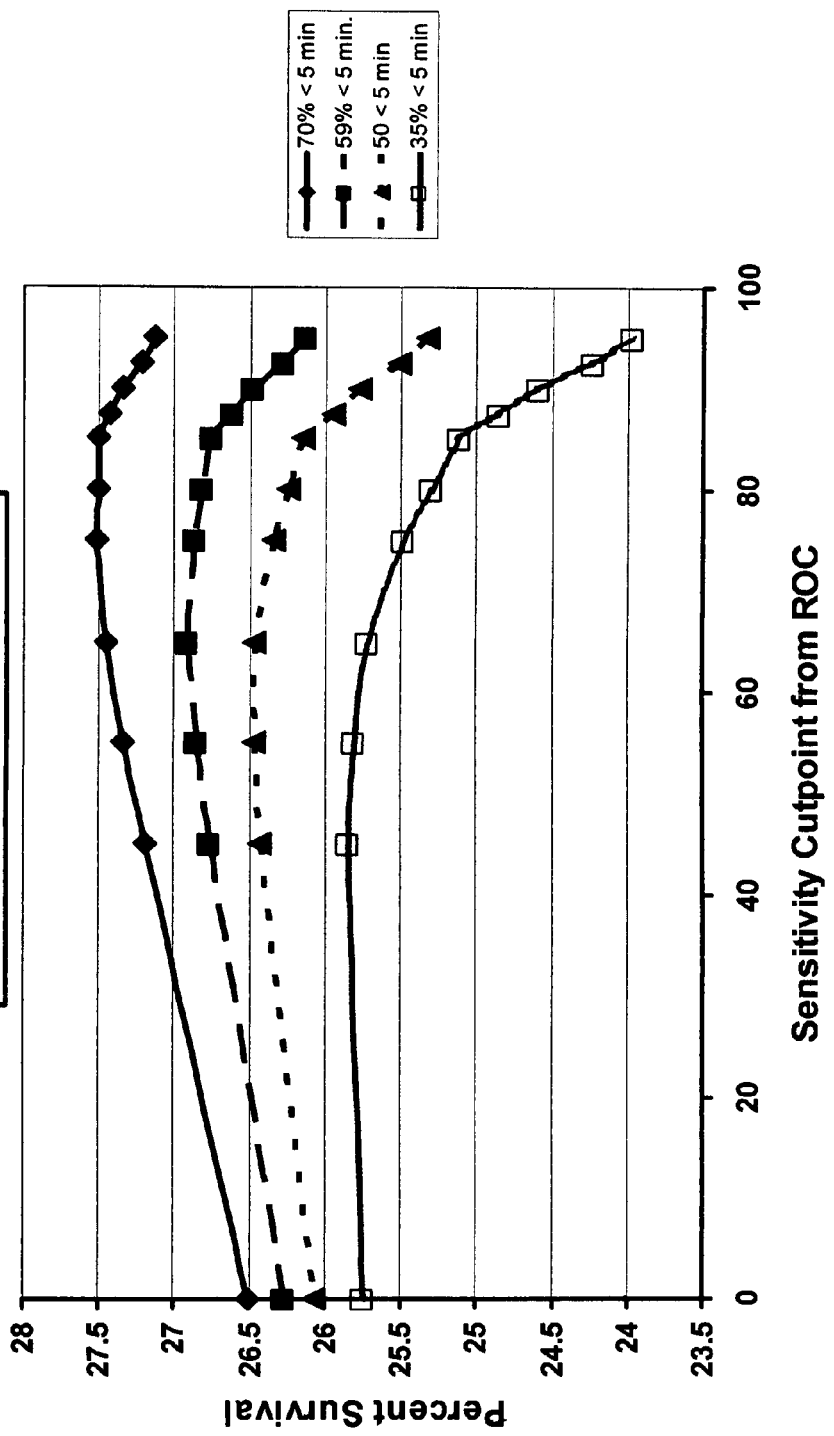
FIG. 7 illustrates the results of the overall survival benefit analysis based on calculating the survival at increasing cutpoint sensitivities (for detecting VF of under 5 minutes duration) varying from 0 to 95%, using the subgroup survival estimates from FIG. 4, and the algorithm of FIG. 15 with assumptions of EMS response times varying from 35 to 70% in order to create four survival curves to be used to determine the optimum cutpoint for which the maximum survival will be achieved.

Finally, using the estimates for survival as described in FIG. 4, survival estimates were calculated in order to compare EMS systems with response times varying from 70% being less than 5 minutes on average, down to 35% having response times less than 5 minutes. This was done as follows. The overall survival for a group of 100 patients was calculated using the subgroup survivals described above for the response times varying from 35% to 70%. This overall survival was calculated at "cutpoints" based on the ROC curve for the LR measure. For a given cutpoint, which would be a value of sensitivity for detecting VF of less than 5 minutes (the TRUE POSITIVES) from the group of all patients with VF of less than 5 minutes, there would also be associated an ability or sensitivity for detecting patients with VF of over 5 minutes duration from the total population of all patients with VF of over 5 minutes. This sensitivity for detecting VF of over 5 minutes would of course vary depending on the cutpoint selected for detecting VF of under 5 minute duration. These are readily taken from the ROC curve data. By calculating the resulting overall survival based on the subgroup survival estimates of the model described above at varying cutpoints (FIG. 7), it is possible to determine which cutpoint is associated with the highest percentage survival for the 100 patients. This will also vary depending on the EMS system response time that is being evaluated. To state it clearly, the overall survival calculated by the model at the various cutpoints will also depend on the known or estimated percentage of the time that EMS responses are less than 5 minutes (some other appropriate time period could also be used). The cutpoint to be selected to achieve maximum survival will vary for each region or group responding to VF cardiac arrest depending on their particular average response time. This serves as a measure of the assumed duration of VF for the patients involved in the model. This leads to the inevitable conclusion that the cutpoint selection for the maximum survival would be a substantial improvement in the art for defibrillation technology. In fact as we will see, the 95% cutpoint used for comparing the different measures above is not the cutpoint that should be used to achieve maximum survival in any of the models for EMS system response times. Much lower cutpoints, near 65%, will provide greater survival in all cases, though the figure will vary depending on the average EMS response time for a given region, locale or group. FIG. 7 shows the curves for systems with varying response times and one may observe that the survival estimate varies with the cutpoint and that the maximum occurs at different cutpoints depending on the EMS system response time being modeled.

The following experimental methods were employed to develop the LR measure and the survival model. Recordings analyzed were from previously published studies in which swine were placed in VF for varying periods of time allowing calculation of measures for over 12.5 minutes. See, Sherman L D, Flagg A, Callaway C W, Menegazzi J J, Hsieh M. Angular velocity: a new method to improve prediction of ventricular fibrillation duration. *Resuscitation* 2004; 60:79 -90; and Menegazzi J J, Callaway C W, Sherman L D, Hostler D P, Wang H E, Fertig K C, Logue E S. Ventricular fibrillation scaling exponent can guide timing of defibrillation and other therapies. *Circulation* 2004; 109: 926 -931. The anesthetic methods and recording techniques are described in detail in these references. In brief, 72 mixed breed swine averaging 25 kg were anesthetized, intubated, instrumented with venous and arterial monitoring devices, and placed in VF with a DC shock. They were allowed to remain if VF for varying periods of time with 45 animals having VF over 5 minutes in duration sufficient to allow recording of the VF through standard lead II ECG leads with preamplification and signal conditioning at 1000 samples/second with no filtering. These were recorded and stored on a dedicated PC for later analysis. The 45 files were then analyzed in their recorded condition at 1000 samples/second without filters for calculation of LAC, LR and other measures for comparison. All recordings were analyzed sequentially using 5 second intervals consisting of 5000 points each for the duration of the recording. 150 such segments were analyzed for a 12.5 minute recording. This was repeated for each of the 45 recordings for approximately 6500 separate calculations for each measure. The recordings were then decimated to 125 samples/second and low pass filtered to exclude frequencies above 62.5 Hz. The calculations were then repeated using sequential 5 second segments consisting of 625 points each. All calculations were done with MAT-LAB using standard functions and were repeated with custom programs written in C++ utilizing standard routines for Fourier analysis. Classification lines for separation of the two dimensional measures (LAC and LR combined) for segments less than 5 minutes from those over 5 minutes at the 95% sensitivity level were performed using two dimensional scatter plots. ROC curves of the LAC and LR were calculated using "Analyse-it for Microsoft Excel" (Analyse-It Software, Ltd., Leeds, England). Survival benefit estimates were then made using sequential cutpoints (for sensitivity to detecting VF duration of less than 5 minutes) that were derived from the LR ROC curve. By using a series of cutpoints between 0 and 95%, each of which was also associated with a specific sensitivity for detecting VF of over 5 minutes duration (as determined by the ROC curve data), a curve of estimated total survival (based on the estimates of survival for each individual subgroup described above) was formed. Finally, the assumptions in the model were then modified to reflect differences in average response times which might be seen in different EMS systems or for other responding groups being modeled (the percentage of cases in which the response times were less than 5 minutes was varied from 35% to 70%) in order to demonstrate the effect of reducing the average EMS response or responder times on the overall survival based on this model. Selection of the maximum of each curve then indicated the highest overall survival and also the cutpoint at which this maximum occurred. This cutpoint could then be used in the LR algorithm to guide therapy to achieve this survival.

Figure 5:
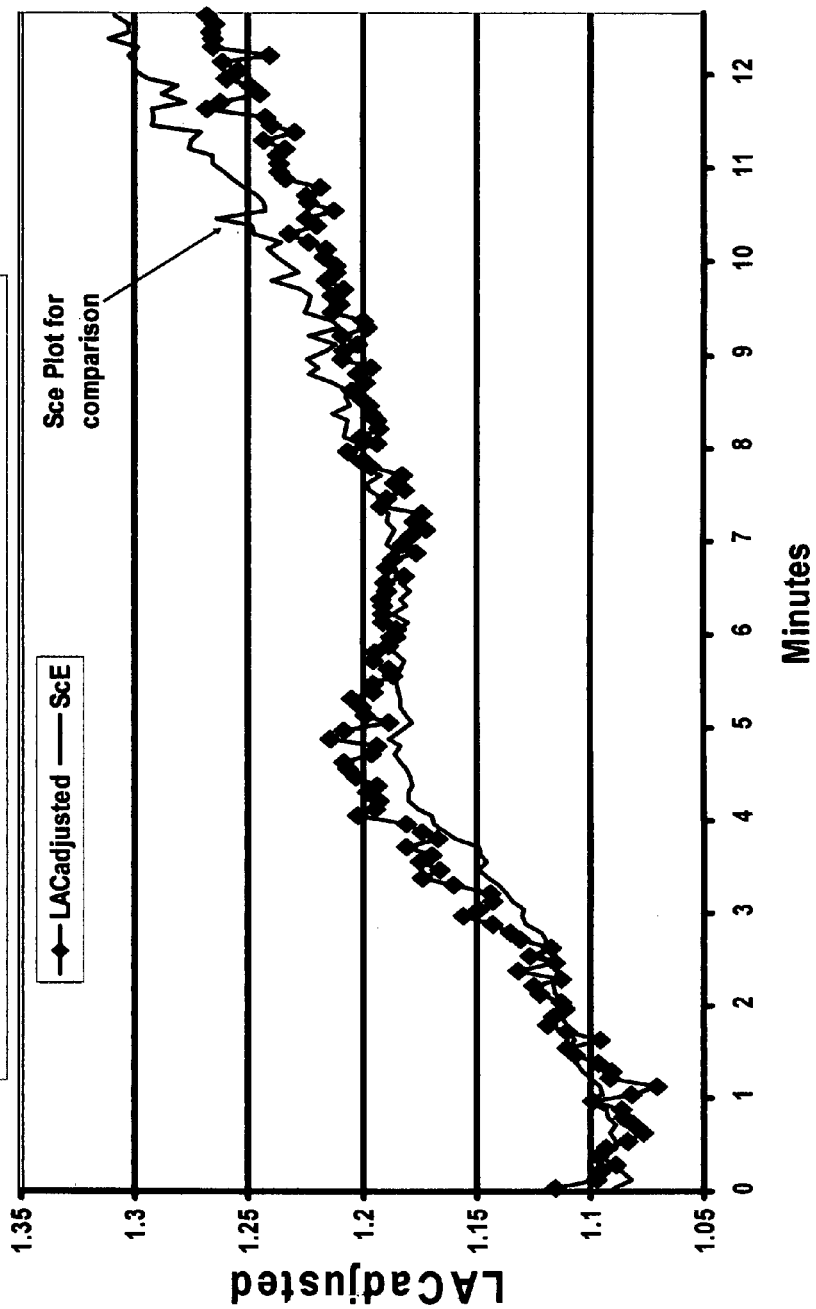
FIG. 5 illustrates the time course of the LAC values which have been transformed to produce the LACadjusted in data from 45 swine recorded at 1000 samples/second with no filtering.
Figure 6:
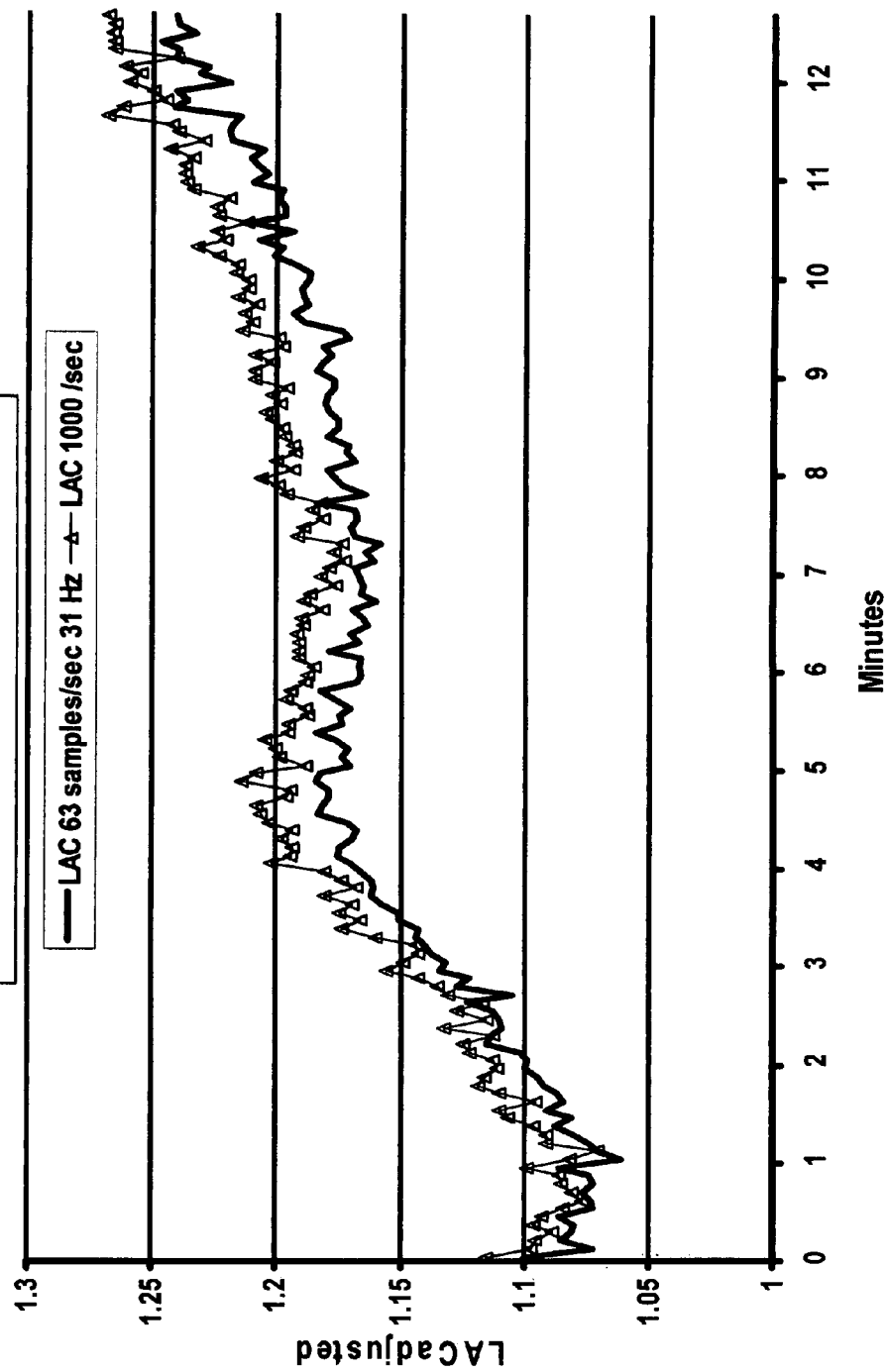
FIG. 6 illustrates the time course of the LACadjusted for VF recorded from 45 swine at 1000 samples/second and unfiltered and the LACadjusted curve from the same recordings decimated to a recording rate of 63 samples/second and filtered to below 31 Hz.

Using these methods, the course of the LAC with transformation to approximate the ScE, called the LACadjusted, is shown in FIG. 5 along with the ScE for the same data recorded at 1000 samples/second for comparison. The LAC at 63 samples/second and low pass filtered below 31 Hz is shown in FIG. 6 to demonstrate its ability to measure self-similarity despite lower sampling rates and filtering.

Figure 8:
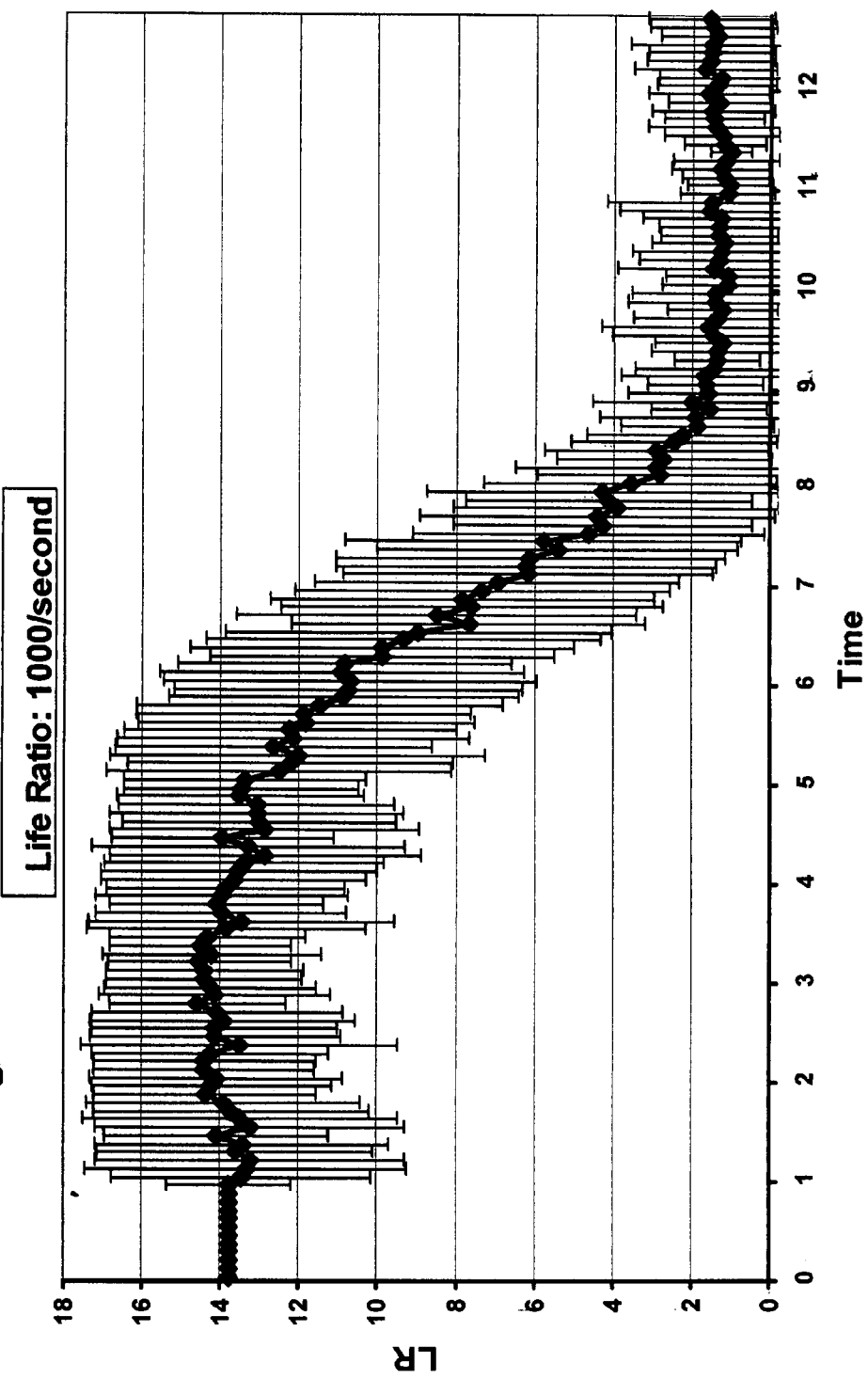
FIG. 8 illustrates the time course of the Life Ratio for 45 VF recordings obtained at 1000 samples/second without filtering.
Figure 9:
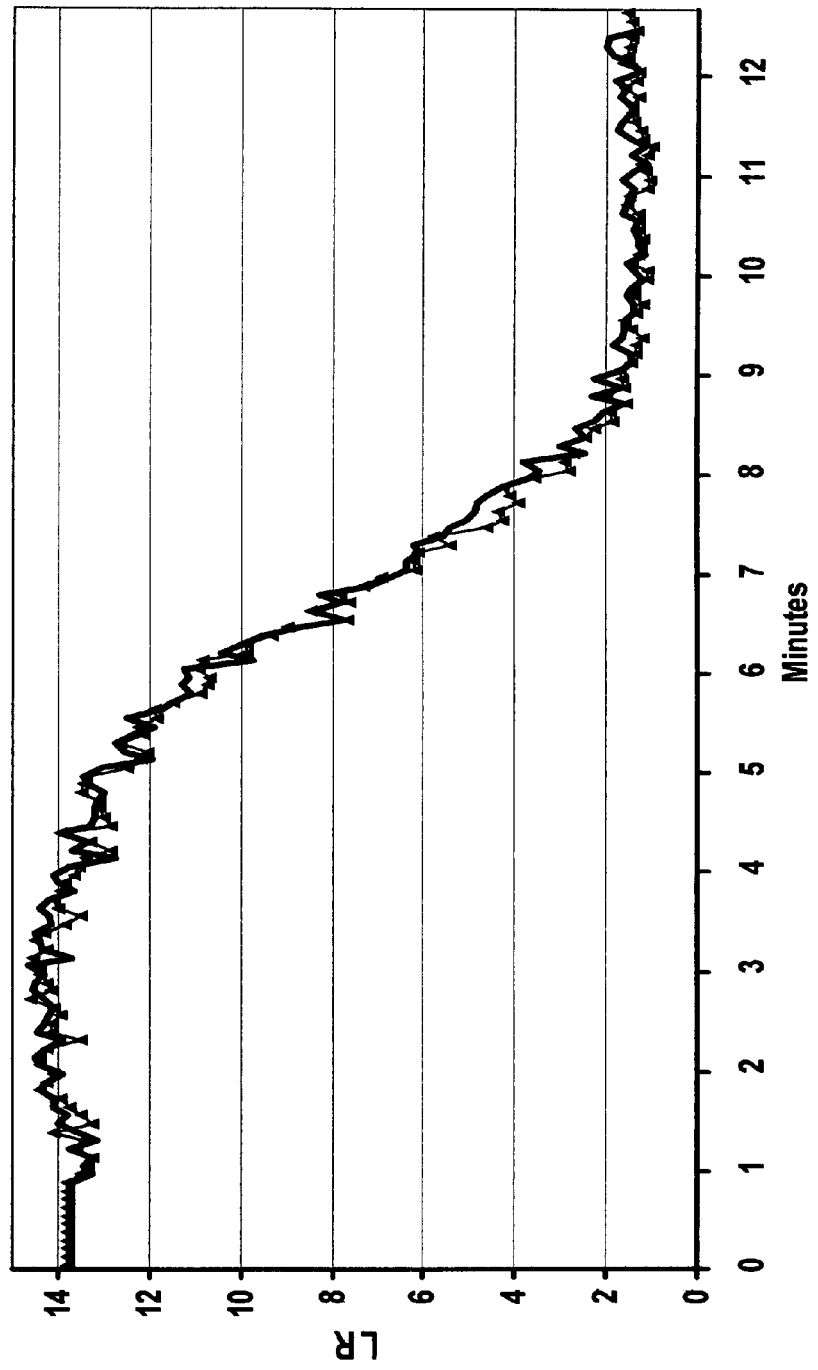
FIG. 9 illustrates the time course of the Life Ratio for 45 VF recordings obtained at 1000 samples/second without filtering and for the same data decimated to recording rates of 125 samples/second and low pass filtered to frequencies below 62 Hz.

The LR is shown in FIG. 8 for the 1000 samples/second unfiltered recordings and in FIG. 9 for 125 samples/second and 62.5 low pass filtered recordings. It is clearly seen to retain its structure and its ability to differentiate VF less than 5 minutes from that over 5 minutes in duration.

Figure 10:
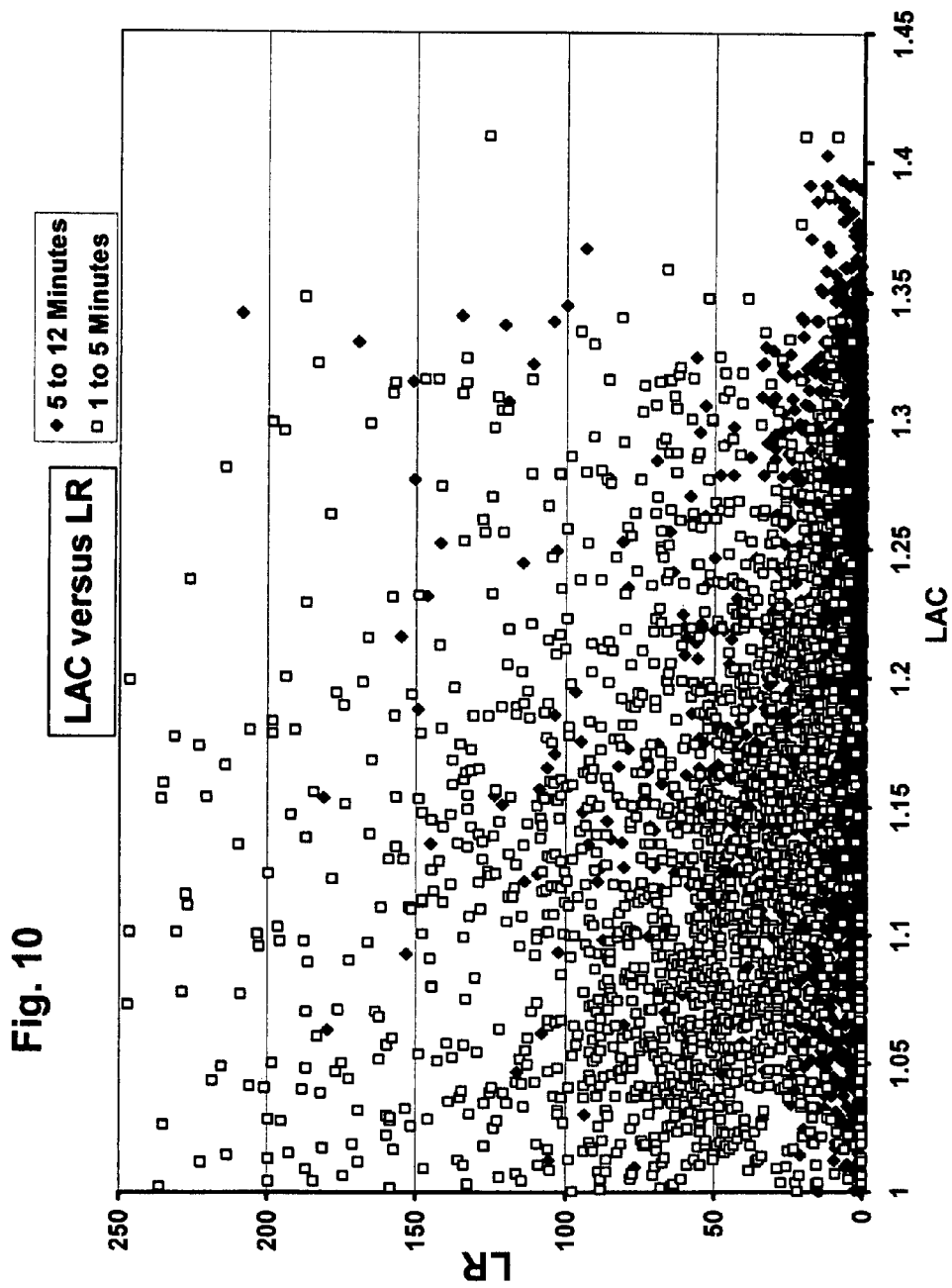
FIG. 10 illustrates the two dimensional distribution of 5 second epochs of VF of less than 5 minutes duration and of over 5 minutes duration in the 45 swine recordings with regard to LR and LACadjusted.
Figure 11:
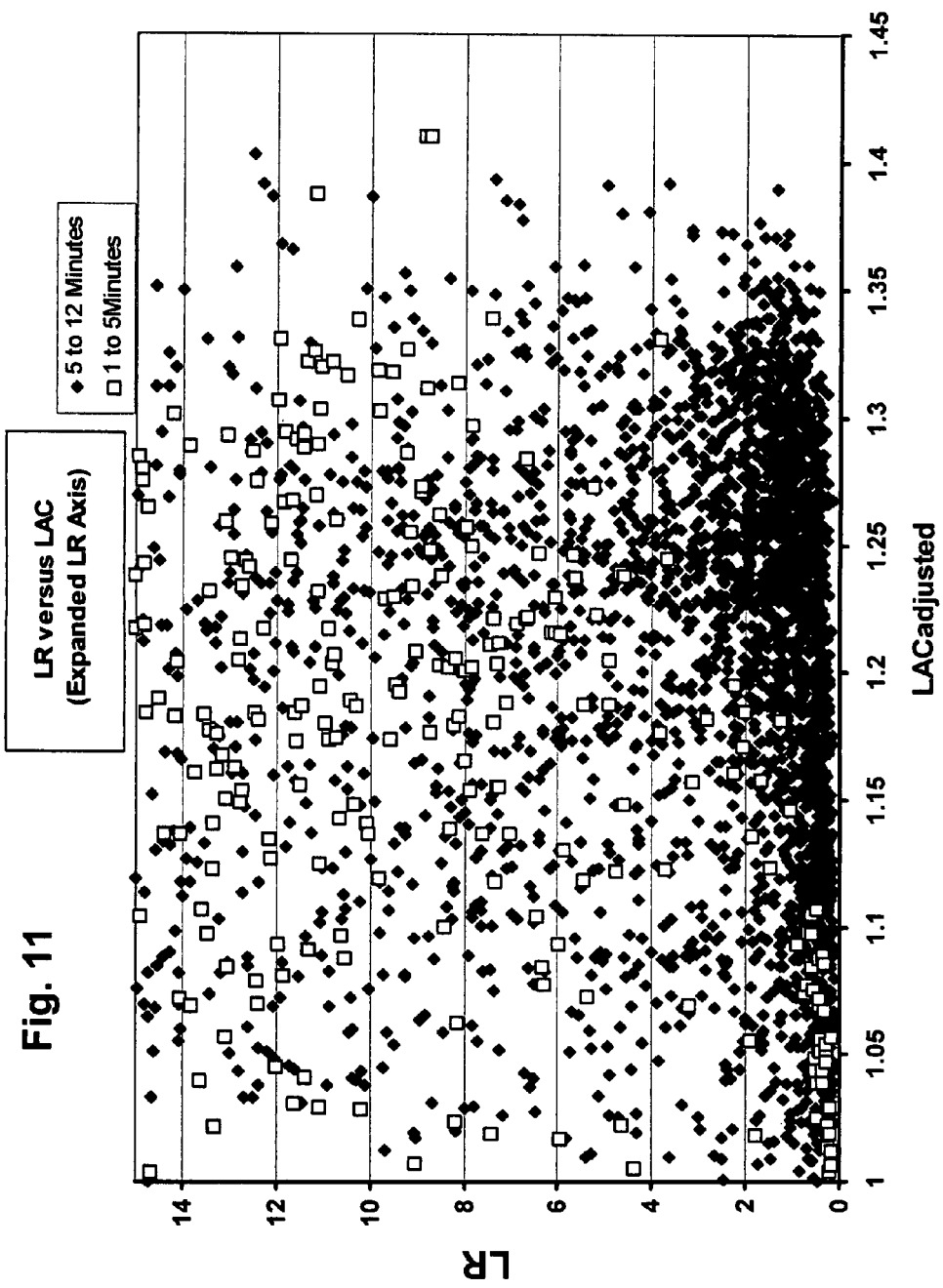
FIG. 11 illustrates the two dimensional distribution of 5 second epochs of VF of less than 5 minutes duration and of over 5 minutes duration in the 45 swine recordings with regard to LR and LACadjusted showing only the LR values up to 15 to expand the lower portion of FIG. 10 for more detailed evaluation.
Figure 12:
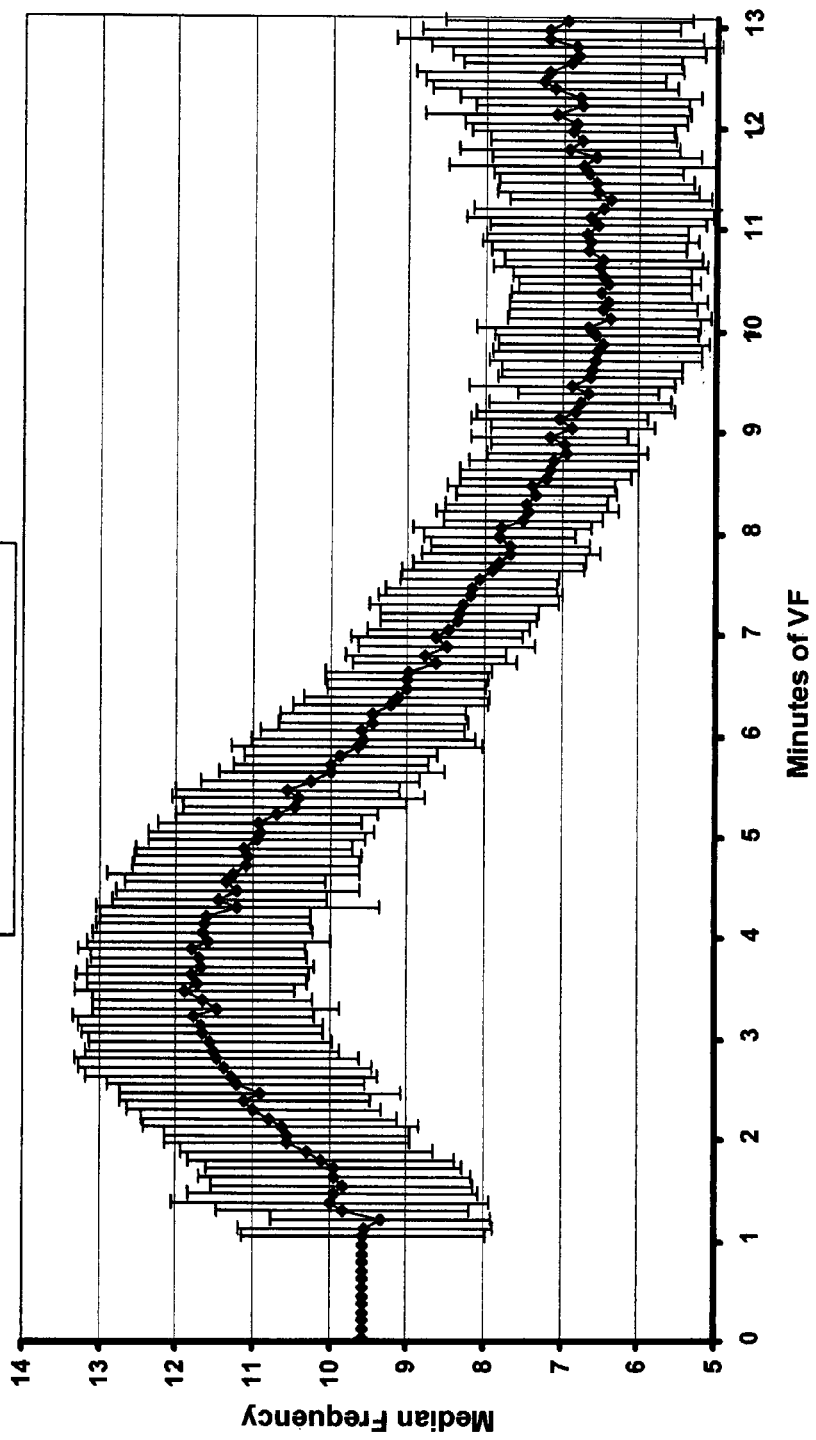
FIG. 12 illustrates the time course of the Median Frequency for the 45 VF recordings obtained at 1000 samples/second without filtering.

For the one dimensional graphical representation of the changes over time the LR was given a maximum value of 15 (values above this were set at 15). This allowed standard deviations to reflect more accurately the relevant variability in the region of interest. For two dimensional comparisons where the LR is combined with the LAC (FIGS. 10, 11) the LR is shown without applying the maximum limit of 15. This method of using a ratio of the two bands was found to be more sensitive to changes in the region of interest, i.e. more sensitive to changes in frequencies at 5 minutes than using an average or weighted average of all frequencies (as is done in obtaining the Median Frequency). The change in the MF over time is shown in FIG. 12 showing the initial low portion which severely compromises its usefulness. The LR method therefore is a significant advance and improvement over taking the average or median frequency because the LR does not have an initial low portion which has values that are the same as values at later time periods. The LR, using a ratio of the high and low frequency bands as described, adds significantly to the ability to separate those waveform segments that are from time periods below 5 minutes from those over 5 minutes. Of course, it is also possible to separate VF with other times, such as segments less than 4 minutes from those over 4 minutes. This is done by adjusting the frequency bands to slightly higher or lower frequencies and this and other variations should be considered embodiments of the present invention.

Figure 13:
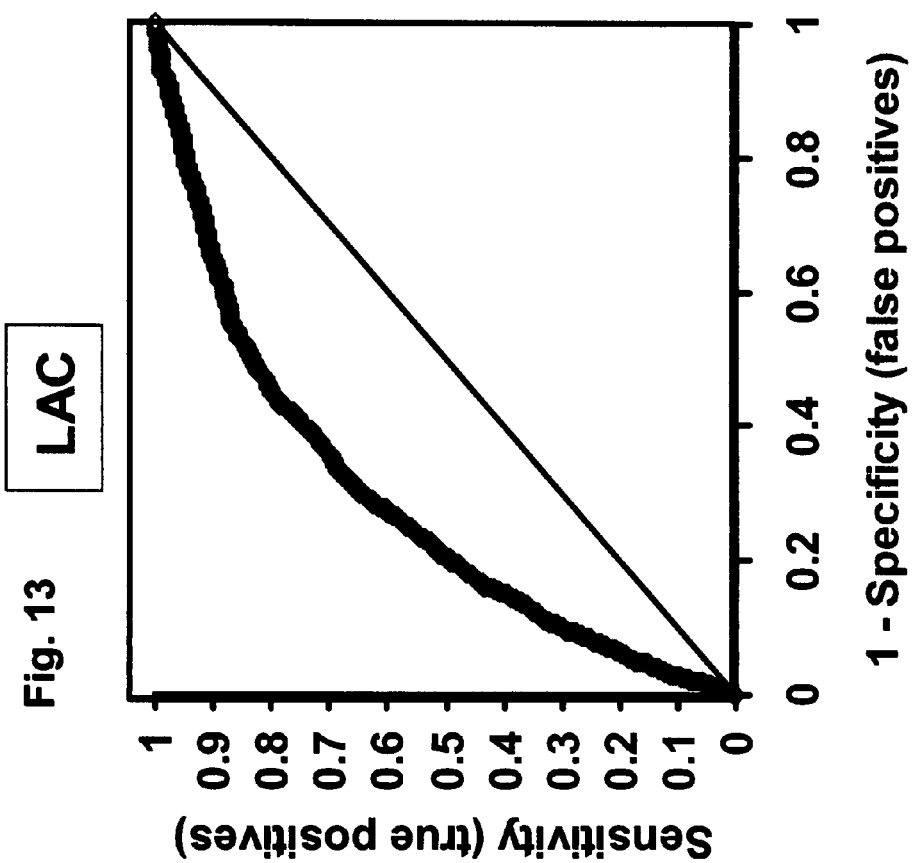
FIG. 13 illustrates the ROC curve for the LACadjusted with the positive result being VF under 5 minutes duration and with an area under the curve of 0.73.
Figure 14:
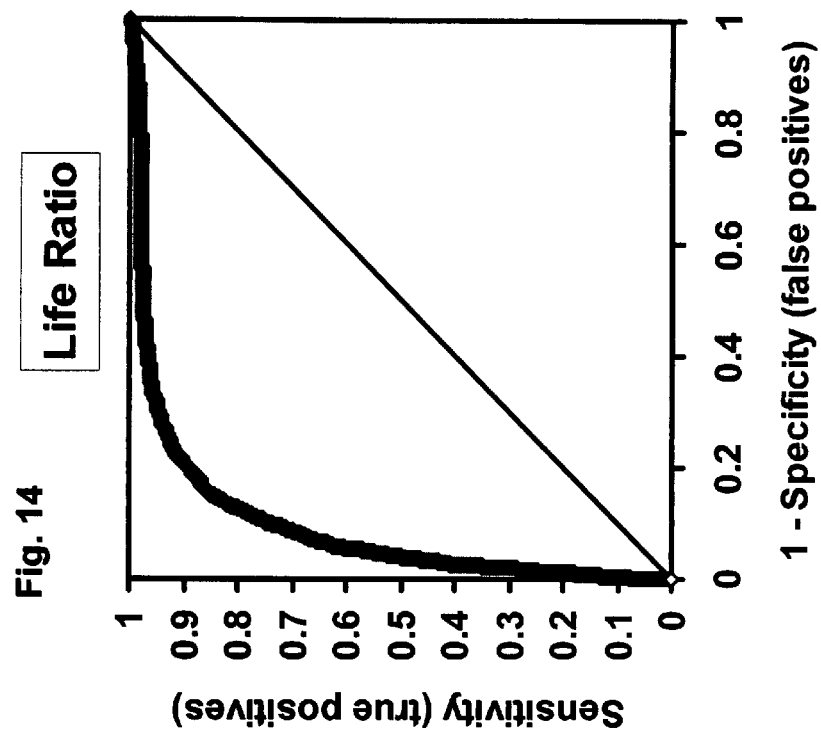
FIG. 14 illustrates the ROC curve for the Life Ratio with the positive result being VF under 5 minutes duration and with an area under the curve of 0.91.

When a sensitivity for detecting TRUE POSITIVES (VF duration of less than 5 minutes) of 95% is used for the LAC, it is possible to detect 20% of those traces which are TRUE NEGATIVES (VF duration of over 5 minutes). The ROC curve for the LAC is shown in FIG. 13 with area under the curve of 0.73. For the LR a sensitivity of 95% for TRUE POSITIVES allows detection of 68% of TRUE NEGATIVES. This is reflected in the ROC curve for the LR (FIG. 14) which has an area under the curve of 0.91.

Since the LR is a powerful discriminating statistic for VF of over 5 minutes, one may ask whether the LAC is able to increase this ability. When combined in 2 dimensional plots (FIGS. 10, 11), the LAC adds a small amount of discriminating ability to the LR. This is achieved by considering all points above the LAC value of 1.34 as being beyond 5 minutes duration regardless of the LR value and also by considering those points with LAC below 1.1 and LR below 0.75 as being outliers and eliminating them from the analysis. Using this strategy, the ability to detect True Negatives (VF over 5 minutes) increases to 72%. This is based on an LR cutoff of 6.5 being used to determine less than 5 minutes status and a LACadjusted cutoff of 1.34 being used to define over 5 minutes of VF. In addition outliers are removed from the analysis, as described above, when LACadjusted is below 1.1 and LR is also below 0.75. The increase in discriminating ability of the LR from 68% without the LAC to 72% with the LAC is small but significant.

Figure 15:
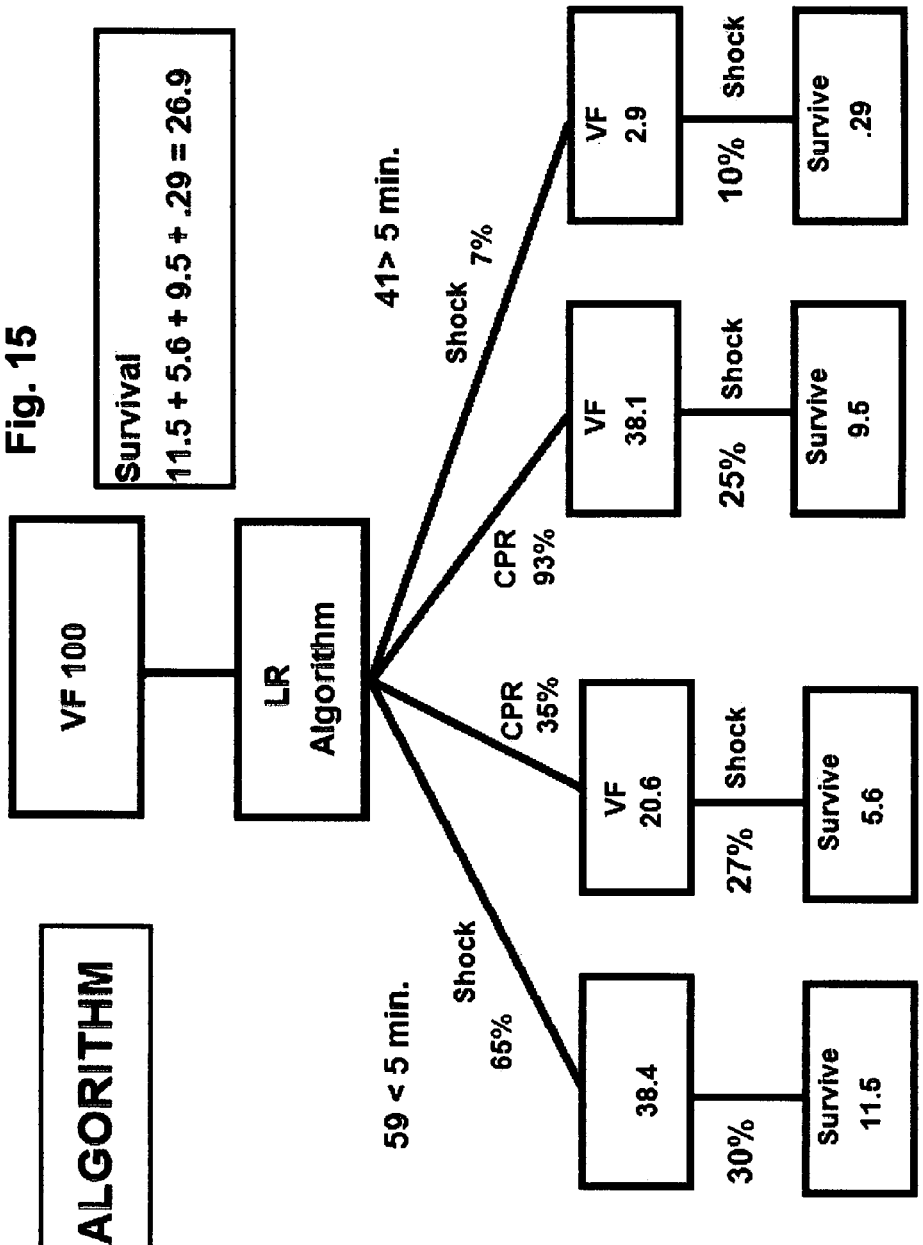
FIG. 15 illustrates the overall survival benefit with the LR algorithm being used to determine therapy (shock first versus CPR first) while using a cutpoint sensitivity (for VF less than 5 minutes) of 65% when 59% of response times to VF are under 5 minutes in the EMS system.
Figure 16:
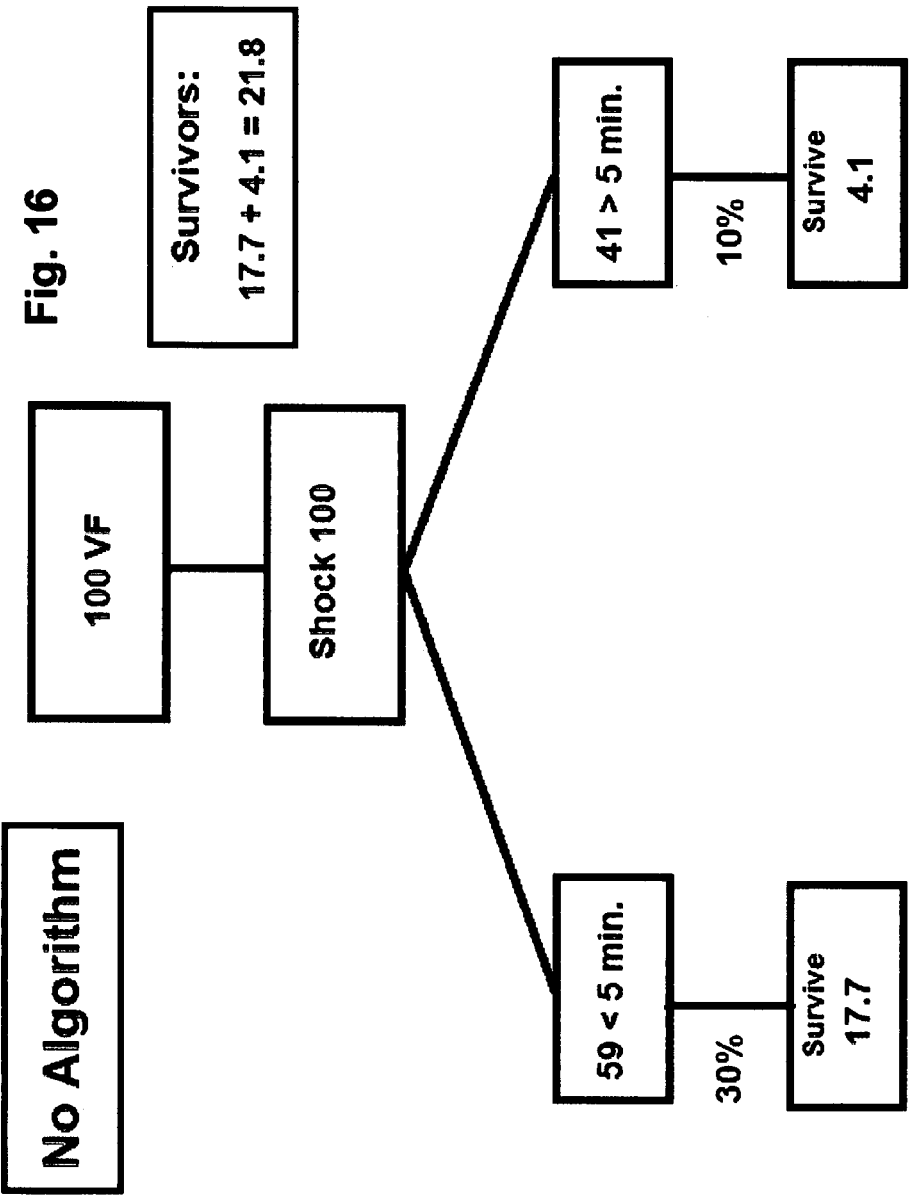
FIG. 16 illustrates the expected survival when no LR algorithm is used to determine therapy but all patients are treated with immediate defibrillation shock.

In order to gauge the survival benefit, we analyzed the effect produced by taking 100 patients through the resuscitation both without and with an algorithm using the LR to separate patients with VF less than 5 minute from those over 5 minutes in duration. A cutpoint of 65% sensitivity for detecting VF of less than 5 minutes was selected because this was found to give the maximum survival for the group with EMS response times of 59% less than 5 minutes (described in detail below, also see FIG. 7). Using this 65% cutpoint, the 65% of the 59 patients with VF less than 5 minutes would be identified and would be given immediate defibrillation with an estimated survival of 30% in this group (FIG. 15). 35% of the 59 patients with VF of less than 5 minutes duration would be given CPR for 3 minutes first and would be estimated to have a slightly reduced survival of 27%. At this cutpoint, 93% of the 41 patients with VF over 5 minutes would be correctly identified and would be given CPR for 3 minutes prior to defibrillation, thus increasing their probability of survival to 25%. Finally, in the remaining 7% of the 41 patients with VF over 5 minutes who receive immediate defibrillation, we would estimate a reduced survival of 10%. Proportions of patients flowing into each arm of the algorithm are based on the two studies described above (59% of responses were under 5 minutes) with the subgroup survival estimates as shown in FIG. 4. Without the algorithm, all 100 patients would be shocked initially and there is a net overall survival of 21.8 patients based on estimates of response times and subgroup survivals (FIG. 16). With the LR algorithm set at 65% sensitivity, there is an overall survival of 26.9, representing 5.1 additional survivors (FIG. 15). This increase of 5.1 over a baseline of 21.8 represents an increase of 23.4% in overall survival.

Because the overall survival calculated is strongly affected by both the percentage of patients who have response times less than 5 minutes for the EMS system being modeled and also by the sensitivity that is selected for the cutpoint, an analysis of these features was carried out as shown in FIG. 7. EMS response times in which 70%, 59% (Cobb/Wik data), 50%, and 35% of responses are under 5 minutes were modeled. The survival resulting from using different "cutpoints" for detecting a given percentage of those with VF under 5 minutes is plotted against survival to show how survival varies with cutpoint selection at each response time. These show several important results. For the two EMS systems from which survival estimates were drawn, Seattle and Amsterdam, 59% of responses were under 5 minutes. For this distribution, the 95% cutpoint is at a 26.1% survival. By using a 65% sensitivity for detecting VF of under 5 minutes duration, overall survival would be increased to 26.9%. If 70% of the response times could be achieved in under 5 minutes, then the 80% cutpoint would produce the highest overall survival of 27.5%. It is envisioned that each EMS system or other user group will input the approximate average percentage of response times under 5 minutes in its area and the subgroup survival data which are representative of the particular system. The EMS system or other group or the algorithm itself as run by the processor would then select the cutpoint to be used based the cutpoint at which the maximum survival benefit occurs on the curve. The use of an algorithm using the LR (possibly also with the LAC) with user inputs as described herein will substantially improve survival from VF and is a very significant improvement in the art as it currently exists. Currently we are not aware of any such overall survival benefit algorithm for use in defibrillators or similar devices.

The use of the ratio of high and low frequency bands as defined for the Life Ratio has increased sensitivity for detecting VF duration of over 5 minutes to approximately 68% when using a 95% cutpoint for VF of less than 5 minutes duration. This is a definite improvement over the Median Frequency and Angular Velocity which are able to achieve only 51% and 60% sensitivity respectively for detecting VF of over 5 minutes duration at the 95% cutpoint. The ability of the LR to distinguish VF over 5 minutes increases to 72% when combined with the self-similarity/amplitude based LAC measure. The technique discriminates patients more likely to respond to immediate defibrillation from those that would benefit from CPR and other therapies prior to defibrillation. The method can be used in currently available defibrillators and AEDs to guide therapy with a projected increase in survival to 26.9% by selecting a cutpoint of 65% for sensitivity in detecting VF of under 5 minutes duration when EMS response times are similar to those in Seattle and Amsterdam. Adjusting sensitivities according to average EMS response times for each local region will also optimize survival. This analysis shows that careful attention must be given to selection of the parameters in each specific EMS system in order to optimize survival.

Figure 17:
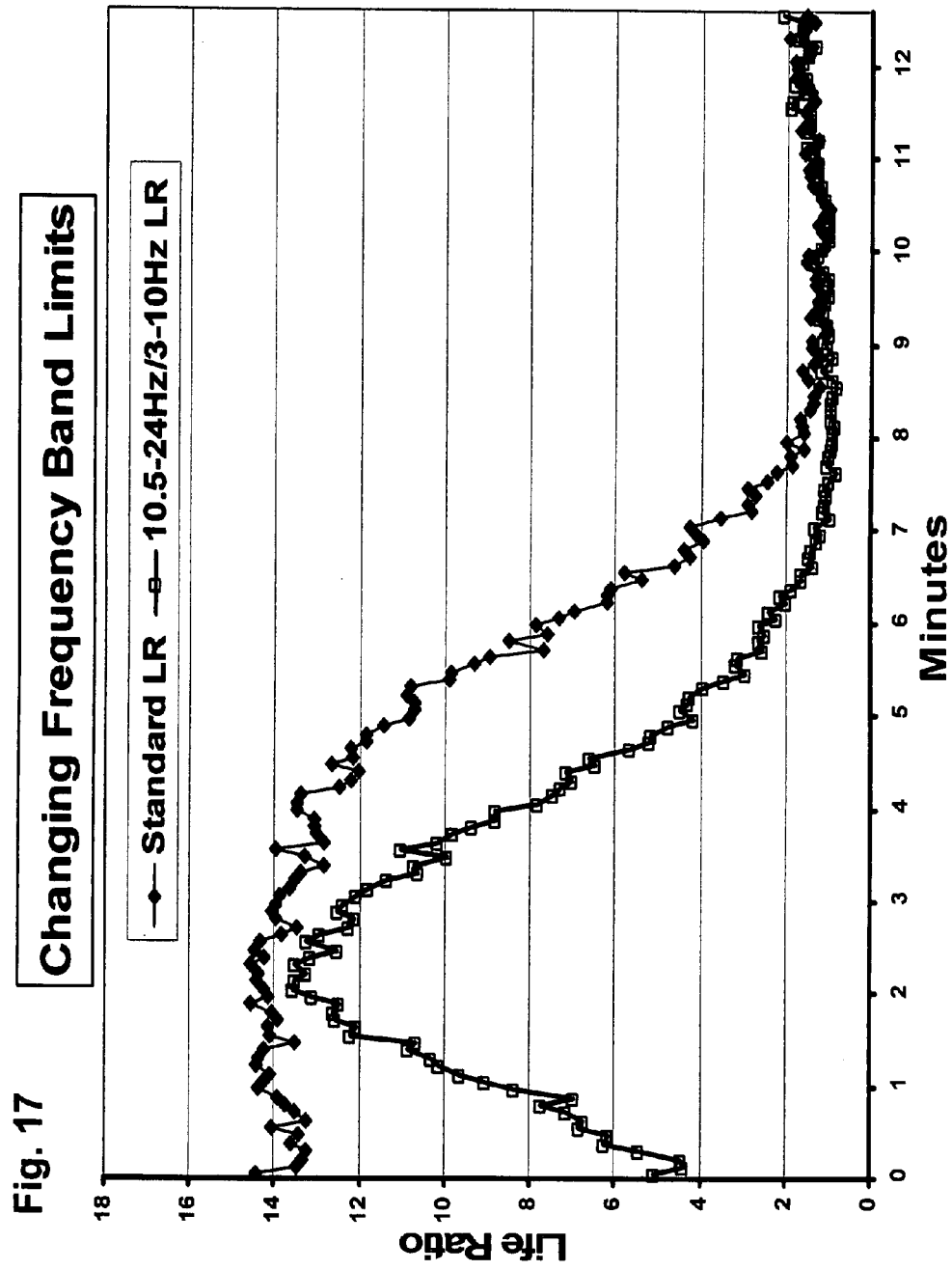
FIG. 17 illustrates the effect on the Life Ratio of changing the range for the high frequency power band to the region 10.5 Hz to 24 Hz and of changing the range for the low frequency power band to the region 3 Hz to 10 Hz demonstrating that the rapid decline occurs 1.5 minutes earlier on average.

We have here described a new measure of the VF waveform, the Life Ratio. The LR method relies on the Fourier transform of the waveform but differs from the average of the frequency spectrum as embodied in the Median Frequency measure by not being an average, but being a ratio with greatly improved ability to discriminate time periods in VF. The LR is also an improvement over the Angular Velocity in that it provides a better separation of the time periods being considered than the AV (68% for the LR compared to 60% for the AV and compared to 51% for the MF). The use of the ratio of high and low frequency bands has two significant advantages over the MF and AV. The first advantage is that it extends the ability to distinguish VF of less than 5 minutes duration from that over 5 minutes in duration from 51% for the Median Frequency and 60% for the Angular Velocity to 68% for the Life Ratio. The second advantage is that by varying the frequency ranges which define the high and low frequency bands, the LR can be altered to select out other time periods or other responses to defibrillation (FIG. 17). It is expected that as the LR is utilized it will be modified and refined. In particular more data will be obtained, specifically, many example waveforms of VF which respond to electric shock with conversion to perfusing rhythms and survival of the patients will be obtained as well as many recordings of waveforms for patients who do not respond will be obtained. These can then be analyzed with varying frequency bands to refine the selection of band widths which separate the two groups. This is different than merely changing the Median Frequency or AV value that would be used as a cutoff for deciding which patients to defibrillate or to perform CPR on. While the LR allows this change of cutoff, the ability to change the frequency bands also directly changes the curves which are used to separate the two groups. Changing the frequency bands allows the period of rapid decline in the LR to be moved to earlier or later times in the curve. For instance, FIG. 17 shows how changing the high frequency band to 10.5 Hz to 24 Hz and increasing the width of the low frequency band to 3 Hz to 10 Hz changes the downsloping portion of the curve so that it occurs approximately 90 seconds before the standard LR measure. This allows one to selectively increase sensitivity for separating out these different time periods. In this application we have chosen to emphasize the 5 minute time period because it appears at this time to be the most clinically relevant. In addition, this method works at the recording rates and filter settings seen in currently used devices.

Because the appropriate treatment of VF is strongly dependent upon its duration, especially when VF duration is approximately 4 to 5 minutes, the improved devices, systems and methods of the present invention to estimate duration of ventricular fibrillation near 5 minutes of duration from a short segment of recorded heart rhythm/ventricular fibrillation provide a significant improvement in the art. Although the methods, devices and systems of the present invention are discussed in terms of a classification system including two classes of ventricular fibrillation (that is, less than 5 minutes duration and greater than 5 minutes duration), a classification system having greater than two classes can be easily developed.

The combination of LR and LAC in several embodiments of the present invention improves the accuracy of VF duration estimates and provides an improved method of characterization of the VF waveform, to, for example, identify states of the waveform and to identify preferred or optimal treatment methodologies associated therewith. The measured LR and LAC are substantially independent of body habitus, electrode position, electrode conductance, myocardial mass, etc.

The combination of LR and LAC in several embodiments of the present invention improves the accuracy of VF duration estimates and estimates of probability of successful defibrillation to a modest extent. The ability to distinguish VF of less than 5 minutes duration from VF of greater than 5 minutes duration in signals acquired at low sampling rates and heavily filtered is also a significant advance in the art. Moreover, it is expected that later time periods will be distinguishable using these and related techniques. This ability allows therapies to be developed which can focus on the different phases of VF. These phases have, for example, been divided into the electrical, the circulatory and the metabolic phases. See, for example, Weisfeldt, M L, and Becker, L B, Resuscitation after cardiac arrest: a 3-phase time-sensitive model, JAMA, 288(23), 3035-8, 2002. Furthermore, the ScE has been shown to be predictive of the probability of successful response to defibrillation attempts in humans, see Callaway, C W, et al., Scaling exponent predicts defibrillation success for out-of-hospital ventricular fibrillation cardiac arrest, Circulation, 2001; 103:1656-61. Since the LAC improves measurements of the same quantities or characteristics measured by the ScE, a combination of the LAC and LR can improve on this predictive ability. The effect of therapies on the myocardium and hence on the VF waveform may be reflected by changes in the LR and LAC so that the timing of defibrillation attempts could be based specifically on the changes in these measures as a response to interventions.

The decrease in LR over time also supports the possibility that this statistic is a measure of the underlying physiology of the myocardium. The decrease in LR over time is consistent with the hypothesis that the reduction in energy stores over time results in a reduction in the conduction velocity and signal frequency, which is then reflected in the decrease in LR. It is expected that the changes in the LR which occur over time and follow the same general pattern as are hypothesized for the 3 phases of VF also reflect underlying physiological changes. It is expected that the LR and the LAC, either individually or applied together, will be instrumental in assessing the underlying cardiac physiology of the myocardium and that they will allow the monitoring of patients in VF in a way that is similar to current methods for monitoring the ECG rhythm in patients not suffering from VF. The effect of treatments that are applied, such as chest compressions, ventilations, epinephrine or vasopressin administration, or other treatments to be developed, could then be followed by observing the change in the LR or the LAC or some combination of them.

Figure 18:
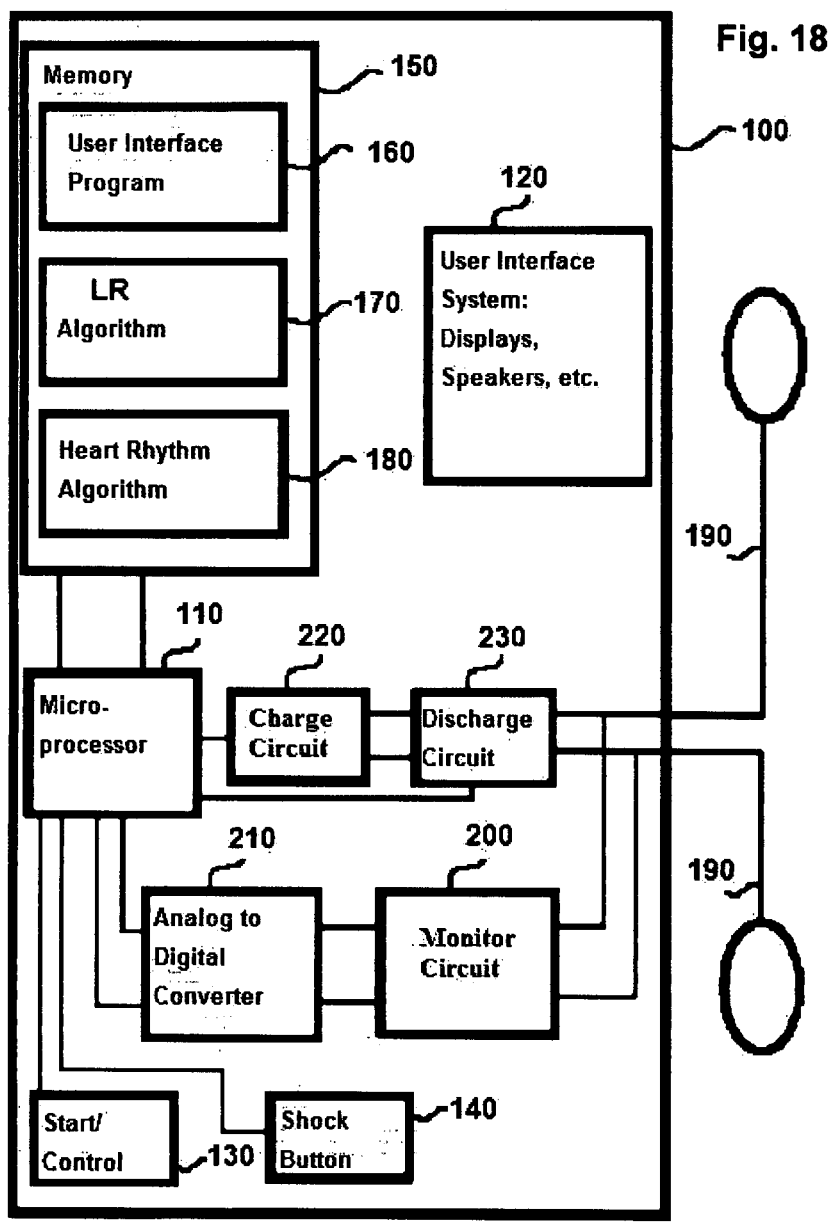
FIG. 18 illustrates an embodiment of the present invention consisting of an automated external defibrillator with display which incorporates a protocol or tool to determine the duration of ventricular fibrillation or the likelihood of success of a defibrillation shock or the cutpoint for maximum overall survival benefit based on the LR or LR and LAC and used to determine therapy.

A treatment methodology, protocol or tool of the present invention (such as illustrated in the figures) can readily be incorporated into an existing defibrillator. In that regard, FIG. 18 illustrates schematically an embodiment of an automated external defibrillator (AED) similar to that disclosed in in U.S. Pat. No. 6,697,671, the disclosure of which is incorporated herein by reference. Another example, of an AED into which the protocols of the present invention can be incorporated is disclosed in U.S. Pat. No. 6,662,046, the disclosure of which is incorporated herein by reference. Commercially available AEDs into which the protocols of the present invention can be incorporated include the LIFEPAK® series of AEDs available from Medtronic Physio-Control Manufacturing Corp. of Redmond Wash.

Although those AEDs are set forth as representative examples of defibrillators into which the protocols of the present invention can be incorporated, one of ordinary skill in the art appreciates that such protocols can be incorporated into virtually any device or system in which heart rhythm is measured.

See FIG. 18: The following is an explanation for the drawing. AED 100 includes a processor (a microprocessor 110 in the illustrated embodiment) which generally controls the operation of the AED 100. The processor used can, for example, be an analog processor or a digital processor, and suitable processors include, but are not limited to: microprocessors, workstations, PC's, hardwired circuitry and the like. Microprocessor 110 is in communicative connection with a user interface system 120, which can include one or more of each of a display, a microphone, a speaker, keyboard or keys, etc. for the input or output of information. A start/control button 130 and a shock button 140 can also be in operative connection with microprocessor 110.

A memory 150 including a user interface program 160 stored therein is also in communicative connection with microprocessor 110. Memory 150 also has stored therein, for example, as part of or in operative communication with user interface program 160 an operation protocol or program 170 based upon the LR or based upon the LR and the LAC as described above. This program 170 also has as part of the operation protocol the ability to select the cutpoint to be utilized based on maximum survival benefit as described above. There would be present in the user interface program the ability for the user to input various estimates of subgroup survival and the average response times for the regional EMS system (or other group) using the device. These values would then be used by the operation program 170 to determine the cutpoint for the LR or LR and LAC values to be used by the operation program. User interface program 160 can, for example, be formatted as described generally in U.S. Pat. No. 6,697,671. In addition, user interface program 160 can, for example, generate visual instructions upon a display of user interface system 120 and/or generate audible instructions transmitted via one or more speakers of user interface system 120. Memory 150 can additionally store a voice recognition software module as known in the art, to enable a user to operate AED 100 and respond to visual and/or audible instructions via voice command rather than using control buttons such as start button 130 and shock button 140.

During operation, the microprocessor 110 analyzes an electrocardiogram (ECG) of a patient using, for example, an automatic heart rhythm algorithm such as disclosed in U.S. Pat. No. 6,697,671 or other algorithm, which is stored in memory 150 to track the heart rhythm of the patient. Currently, such algorithms are functional, for example, to identify whether the patient is experiencing a shockable heart rhythm, such as ventricular fibrillation. Such algorithms are used, for example, in the LIFEPAK®500 defibrillator available from Medtronic Physio-Control Corp. Other such algorithms include those designed to comply with standards promulgated by the Association for the Advancement of Medical Instruments (AAMI). ECG signals analyzed by heart rhythm algorithm 180 are collected by the electrodes 190 and communicated through monitor circuit 200 to an analog-to-digital converter 210 which then passes the digitized signals to microprocessor 110. Under current practice as described, for example, in U.S. Pat. No. 6,697,671, if microprocessor 110 detects a shockable rhythm, microprocessor 110 causes a charging circuit 220 to generate a current causing a storage capacitor (not shown) to charge in preparation for delivery of a defibrillation shock to the patient. When the capacitor is fully charged, and delivery of the defibrillation shock is initiated, a discharge circuit 230 in operative communication with microprocessor 110 and charge circuit 220 discharges the defibrillation shock to electrodes 190 for application of the defibrillation shock to the patient.

The present invention provides a significant advance in the art by providing operation algorithm 170 (which can, for example, operate in conjunction with heart rhythm algorithm 180) based upon the LAC or based upon the LR and the LAC and incorporating a survival benefit algorithm based upon user input variables specific to the geographic region, locale and user group as described above. In accordance with the procedures described above, such an operation protocol can be used to characterize the ventricular fibrillation waveform and/or to determine the state of ventricular fibrillation. The determined character or state of the ventricular fibrillation waveform can be used to determine the likelihood of success of defibrillation (as defined, for example, by the survival benefit analysis described above) to, for example, cause AED 100 to automatically deliver a defibrillation shock if the determined probability is greater than a predefined threshold (described as the "cutpoint" above) or to prevent shocking by AED 100 or warn against shocking if the probability of success of a defibrillation shock is less than a defined threshold or cutpoint. If the success of defibrillation is less than a defined threshold or cutpoint, then the AED can also advise the rescuer to begin CPR or an alternative treatment rather than to shock.

When used in connection with monitor defibrillators such as used by highly trained individuals, the treatment protocol of the present invention can provide information as to the duration of ventricular fibrillation or as to the state of ventricular fibrillation to allow, for example, a physician to determine a proper treatment associated with that duration or phase. If, for example, the state of the ventricular fibrillation is consistent with the circulatory phase (as described by Weisfeldt and Becker, see reference above), then CPR may be performed prior to shock. If the ventricular fibrillation is consistent with the metabolic phase, then the advanced life support caregivers can establish IV access and give drugs which would improve or treat the metabolic derangements present prior to shock being delivered. The defibrillator system can also recommend a treatment based upon the probability of a shock or other treatment being successful or on the basis of the overall survival benefit. A recommended treatment or therapy other than defibrillation (should the probability of success of defibrillation or of overall survival benefit be determined by the system to be below a threshold value) can include, but is not limited to: (1) reperfusion; (2) re-oxygenating the fibrillating heart of the patient; (3) employing a period of cardiopulmonary resuscitation (CPR); (4) employing artificial perfusion; (5) employing one or both of CPR and ventilating the patient and (6) drug administration. Such alternative therapies can be followed by defibrillation, the application and timing of which can be recommended by the system of the present invention based, for example, upon the likelihood of success or improvement in overall survival benefit thereof.

For experienced users, the time course of the character or state of the VF waveform and of the calculated probability of success or improvement in overall survival benefit of a treatment can also be plotted to indicate the progression of the patient's cardiac condition, and to track the response to interventions such as medications or CPR. This relates to the use of the device to monitor ventricular fibrillation and to provide a continuous measure of the state of the myocardium. In this way the measurements may be provided to the experienced user to indicate the effect of interventions as they are delivered. Thus, for instance, the user may use the measure, or some combination of the LR with the LAC combined with the survival benefit analysis for selection of cutpoint, to determine when the interventions provided have been sufficient to cause the myocardium to be sufficiently receptive to a defibrillating shock so that there is a high probability of success or improvement in the overall survival benefit (above some predetermined threshold or cutpoint). This could be done through any of several methods, including a visual display of a number representing the measure, a bar graph representing the magnitude of the measure, or graph charting the progression of the measure over time, or a bar graph representing the probability of successful defibrillation and/or the overall estimated survival benefit.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

COMPUTER CODE LISTING

MATLAB Code for Life Ratio includes Code for LAC:

```
function [dat] = FileManip1 (fname)
%This Function will calculate the FourierPowerSpectrum
%for 625 points or 5 seconds of data at 125 samples/sec
%and calculate a frequency ratio of
%the upper and lower spectrum called the Life Ratio.
%
%
%
%
fname='Dec125Filt62hzShortpig';
%Enter the name of the base file when
%running a series of files
```

-continued

```
ss=[ fname '.LRtest1625record4' ];
%This is the printfile name for
%results, set back to SHORTpig for
%the full series to collect results in
%rows for excel sheet
ssss=[ fname '.Fourier49C' ];
        fid2 = fopen (ss, 'w');
        fprintf (fid2, '%s \n', fname);
        fclose (fid2);
for pignum=1:47 %only used when running a series
fname1=[fname int2str (pignum)];
fname1='testpig1.txt';   %placed here if only running the one file,
                         %"testpig1.txt"
ECGData=[];
ECGData2=[];
autoco=[];
logabstot=[];
pointnumber=625;
widthf=625;%widthfactor
setfile=1;
ECGData=load (fname1, '-ascii');
length1=length (ECGData);
epochnum=fix (length1/pointnumber);
for epoch=12:epochnum-2
%will set to start at 1 minute to eliminate artifact
    ECGData2=ECGData;
    %%%%%%%%%%%%%%%%%%%%%%%%%%%%%%%%%%%%%%%%%%%%%%%%%%%%%%
    %%%CENTERING
    samptot=0;
        icount=(pointnumber*epoch) +1;
        jcount=((pointnumber*epoch) +widthf);
        samptot=sum(ECGData((icount) : (jcount)));
    sampmean=samptot/widthf;
ECGData((icount) : (jcount))=ECGData((icount) : (jcount)) - sampmean;
    %%%%CENTERING DONE
    %%%%%%%%%%%%%%%%%%%%%%%%%%%%%%%%%%%%%%%%%%%%%%%%%%%%%%%
    %%%%%%%%%%%%%%%%%%NOW DO THE CALCULATIONS
    %%%%%%%%%%%%%%%%%%LAC calculations
    autocotot=0;
      autoco=autoco.*0;
        for k=1:60
autocotot=sum(ECGData((icount) : (jcount-1-
k)).*ECGData((icount+k) : (jcount-1)));
autoco(k)=abs((autocotot/((625)-k))*10000000.0);
    %this codes for the increasing to positive ranges, not
    %needed
                autocotot=0;
    end
                abstot=0;
                abstot=sum(autoco);
                    logabstot (epoch+1)=log10 (abstot);
        %%%%%%%%%%%%%logabstot is the LAC%%%%%%%%%%%%%%%
    %%THIS IS THE LACadjusted CONVERSION
    logabstot (epoch+1)=1.74-(logabstot (epoch+1)/6.55)
%%%%%%%%%%%% logabstot is the LAC%%%%%
    if logabstot (epoch+1)< .91
                logabstot (epoch+1)=1.40999;
            end
        if logabstot (epoch+1) > 1.41
                logabstot (epoch+1)=1.40999;
        end
```

```
%%%NOW DO THE FFT calculations%%%%%%%%%%%%%%%%%%%%
Y=fft( ECGData((icount) : (jcount)),512);
Pyy=Y.*conj (Y)/512;
lowsum=0;
highsum=0;
lowsum=sum (Pyy(12:20));
highsum=sum (Pyy(32:96));
Ratio=(highsum/lowsum);
%if Ratio > 15 %2.5    %This is to place the 15 limit when
                       %doing curves with SD calc. see text
    %Ratio=15.00001;%2.5;
    %end
FreqRatio (epoch+1)=(Ratio);         %%%RATIO AND FreqRatio are the
                                     %%%"LifeRatio" results
    PowerS=abs (Pyy);
    PowerSum=sum (PowerS);
if 1==2%mod(epoch+1,5)==0%may use for visualization of power
                       %%%spectrum
    %hh2=figure;
    %plot (ECGData ((icount) : (jcount)));
    f=125* (0:256) /512;
    hh=figure;
    plot(f,Pyy(1:257))
    grid on
    axis ([0 25 0 .06])
    title (['power total='num2str((lowsum+highsum)) ' with
FreqRatio=' num2str (FreqRatio (epoch+1)) ]);
    xlabel ('frequency (Hz)')
pause(.2)
end
%%%%%%%%%%%%%%%%%%%%%%%%%%%END CALCS
%%%%%%%%%%%%%%%%%%%%%%%%%%%%%%%%%%%%%%%%%%%%%%
if 1==2;%mod (epoch+1, 199)==0    %may use to see ECG and LAC
                                  %result
    g=figure;
    plot (ECGData ((icount) : (jcount)));
    grid on
    startSecs=(((epoch+1-1) *pointnumber) +1);
    endSecs=(((epoch+1-1) *pointnumber) + (250));
    title([int2str(startSecs) 's with' ' LAC=']
    pause(.2)
    hh=figure;
    plot (autoco);
    grid on
    title([int2str(startSecs) 's' ]);
    pause(.2)
        end
        ECGData=ECGData2;
%%%%%%%%%%%%PRINT THE RESULTS to a file in various formats
    if (epoch)==12
        fid2 = fopen (ss, 'a');
        fprintf(fid2, '%s \n', fname1);
        fclose(fid2);
    end
        fid2 = fopen (ss, 'a');
fprintf(fid2,' %g \t%g \t%g
    \n',epoch+1, logabstot (epoch+1), FreqRatio (epoch+1) );
        fclose (fid2);
        %%%%%%%%%%%%%END OF PRINT
        end %end of (epoch+1)=1:epochnum-2 loop
    if 1==2
        hh=figure;
        plot (FreqRatio);
        grid on
        %axis ([0 180 0 5])
        title ([ ' Pig' num2str(pignum) ]);
        pause (.02)
        hh2=figure;
        plot (logabstot);
        ylim ([1 1.4]);
        pause (.02)
    end
```

```
        set file=1;
        fid2=fopen (ss, 'a');
        fprintf (fid2, ' \n ');
        %fid3=fopen (ssss, 'a');
        %fprintf(fid3, ' \n ');
        %fclose(fid3);
        fclose(fid2);
        FreqRatio=FreqRatio. *0;
        logabstot=logabstot. *0;
    end
```

This is the end of the MATLAB code section, the C+ code section follows.

C+ Version of Code for Life Ratio

This is the C++ code for a function "LifeRatio" that utilizes the "Numerical Recipes in C" code library and can perform the calculations to produce the Life Ratio. It uses a data set of points in "at" of type "attractor_ptr" which is a set of 625 voltage values from the sample of VF from which the LR will be calculated.

```
double LifeRatio(attractor_ptr at)
{
#define NRANSI //see Numerical Recipes in C for details
#define SWAP(a,b) tempr=(a) ; (a)=(b) ; (b)=tempr
#define WINDOW(j,a,b) (1.0-fabs ((((j)-1)-(a))*(b)))
                    /* Bartlett */
#define NR_END 1
#define FREE_ARG char*
#define M 256      // this is a setting for the discrete Fourier
                   //transform to be used.
#define TRUE 1
#define FALSE 0
FILE *infile, *outfile;
FILE *f;
static char *goo=".LifeRatio2";
char filnam[128]="tempattract";
int a,i, fct;
outfile=fopen(filnam, "w");
char outfilename[256];
sprintf(outfilename, "LRmatrix.MPCtest2");
for (i=1;i<=625;i++)
{
    fprintf(outfile, "%f \n", at->data[3*i]);
}
fclose(outfile);
    double    CentroidFreq=0.0;
    double    sump=0.0;
    double    sumfxp=0.0;
    double lowsum=0.0;
    double highsum=0.0;
    double Ratio=0.0;
    int j,k,ovrlap;
    float *p, *q;
    FILE *fp;
    p=vector(1,M);     //vector is a Numerical Recipes
                       //defined function
    q=vector(1,M);
    if ((fp = fopen(filnam, "r")) == NULL)
        nrerror("Data file not found\n");
    strcat(filnam,goo);
    k=8;
    ovrlap=TRUE;
    spctrm(fp,p,M,k,ovrlap);      //this is a Numerical Recipes
                                  //routine, see below
    fclose (fp);
        sump=0.0;
        sumfxp=0.0;
        lowsum=0;
        highsum=0;
```

```
f = fopen(outfilename, "a");
fprintf(f," \n %s \t ",at->filename2);
for (fct=1;fct<=16;fct++)
        {   sump=0.0
            sumfxp=0.0;
            lowsum=0;
            highsum=0;
for (j=0;j<=51;j++)  //REMEMBER TO RESET THIS IF YOU GO
            //HIGHER THAN 51
            {
//          printf("%3d \t %13f \n",j,p[j]);
//          fprintf(outfile," %13f \t",p[j]);
//THESE ALLOW A PRINTOUT OF FREQUENCIES IF UNCOMMENTED
            if ((j>2) && (j<=((13+fct)))) //((j>11) && (j<21))
                {
                    lowsum = lowsum + p[j];
                }
                else
                if ((j>=((13+fct))) && (j<50))
                    //((j>31) && (j<97))
                    //Can change ranges
                    //depending on which FFT used (512,4096)
                {
                    highsum = highsum + p[j];
                }
                //sumfxp=sumfxp+(p[j] * (j-1));
                //sump=sump+p[j];
            }
Ratio=(highsum/lowsum); //NOTE "RATIO" IS LifeRatio////////
//if (Ratio > 15) { Ratio =15; }  //This sets 15 limit for
                                  //SD calcs
            fprintf(f," %13f \t",Ratio);
//          printf("Median Freq = \t %f \t \n", (sumfxp/sump));
//          fprintf(outfile, " %f \t \n", (sumfxp/sump));
//          CentroidFreq= (sumfxp/sump) ; //can be uncommented to
//          see the MF for comparison, etc.
            sump=0.0;
            sumfxp=0.0;
            lowsum=0;
            highsum=0;
            a=0;
            }
        free_vector(q,1,M);
        free_vector(p,1,M);
        //fprintf(f," \n");
        fclose(f);
        return Ratio;       //THIS IS THE LIFE RATIO
}
//THE FOLLOWING ARE THE SPECIFIC "NUMERICAL RECIPES IN C"
//FUNCTIONS THAT ARE USED TO PRODUCE THE FAST FOURIER //TRANSFORM
CALCULATION IN THE C+ VERSION
void spctrm(FILE *fp, float p[], int m, int k, int ovrlap)
{
        void four1 (float data[], unsigned long nn, int isign);
        int mm,m44,m43,m4,kk,joffn,joff,j2,j;
        float w,facp,facm,*w1,*w2, sumw=0.0,den=0.0;
        mm=m+m;
        m43=(m4=mm+mm) +3;
        m44=m43+1;
        w1=vector(1,m4);
        w2=vector(1,m);
        facm=m;
        facp=1.0/m;
        for (j=1;j<=mm;j++) sumw += SQR(WINDOW(j,facm,facp));
        for (j=1;j<=m;j++) p[j]=0.0;
        if (ovrlap)
            for (j=1;j<=m;j++) fscanf(fp,"%f",&w2[j]);
        for (kk=1;kk<=k;kk++) {
            for (joff = -1;joff<=0;joff++) {
                if (ovrlap) {
for (j=1;j<=m;j++) w1[joff+j+j]=w2[j];
                    for (j=1;j<=m;j++) fscanf(fp,"%f",&w2[j]);
                    joffn=joff+mm;
                    for (j=1;j<=m;j++) w1[joffn+j+j]=w2[j];
                } else {
                    for (j=joff+2;j<=m4;j+=2)
                        fscanf(fp, "%f", &w1[j]);
                }
            }
```

```
            for (j=1;j<=mm;j++) {
                j2=j+j;
                w=WINDOW (j, facm, facp);
                w1[j2] *= w;
                w1[j2-1] *= w;
            }
            four1 (w1,mm,1);
            p[1] += (SQR(w1[1])+SQR(w1[2]));
            for (j=2;j<=m;j++) {
                            j2=j+j;
                p[j] += (SQR(w1[j2])+SQR(w1[j2-1])
                            +SQR(w1[m44-j2])+SQR(w1[m43-j2]));
                }
            den += sumw;
        }
        den *= m4;
        for (j=1;j<=m;j++) p[j] /= den;
        free_vector(w2,1,m);
        free_vector(w1,1,m4);
}
void four1(float data[], unsigned long nn, int isign)
{
    unsigned long n,mmax,m,j,istep,i;
    double wtemp,wr,wpr,wpi,wi,theta;
    float tempr,tempi;
    n=nn << 1;
    j=1;
    for (i=1;i<n;i+=2) {
        if (j > i) {
            SWAP(data[j],data[i]);
            SWAP(data[j+1],data[i+1]);
        }
        m=n >> 1;
        while (m >= 2 && j > m) {
            j -=m;
            m >>= 1;
        }
        j += m;
    }
    mmax=2;
    while (n > mmax) {
        istep=mmax << 1;
        theta=isign* (6.28318530717959/mmax);
        wtemp=sin(0.5*theta);
        wpr = -2.0*wtemp*wtemp;
        wpi=sin(theta);
        wr=1.0;
        wi=0.0;
for (m=1;m<mmax;m+=2) {
        for (i=m;i<=n;i+=istep) {
            j=i+mmax;
            tempr=wr*data[j]-wi*data [j+1];
            tempi=wr*data[j+1]+wi*data[j];
            data[j]=data [i]-tempr;
            data[j+1]=data [i+1]-tempi;
            data[i] += tempr;
            data[i+1] += tempi;
        }
        wr=(wtemp=wr) *wpr-wi*wpi+wr;
        wi=wi*wpr+wtemp*wpi+wi;
    }
    mmax=istep;
    }
}
#undef SWAP
#undef WINDOW
#undef NRANSI
///////////////////////END OF PROGRAM LISTING//////////////////////////
```

What is claimed is:

1. A method of determining a state of ventricular fibrillation comprising:

measuring the rhythm of the heart during ventricular fibrillation for a period of time;

performing calculations to produce a discrete fourier transform from the series of voltage values that make up to measured heart rhythm; summing the power at each frequency for two frequency bands, a low frequency band and a high frequency band; determining a first value related to to high and low frequency bands by taking the quotient of the high frequency power band summation and the low frequency power band summation and naming this quotient the life ratio; and determining the state of ventricular fibrillation by relating the first value to the state of ventricular fibrillation.

2. The method of claim 1 further comprising:
determining a second value which is a logarithm of the absolute correlation of the ventricular fibrillation heart rhythm for the period of time, the step of determining the state of fibrillation including the step of relating at least one value of the first value and the second value to the state of fibrillation.

3. The method of claim 2 further comprising:
a user determined estimate of the percentage of cases for which ventricular fibrillation duration is less than a predetermined time period for the particular user group; the estimate being input into the system by the user; a user determined estimate of survival for patients with ventricular fibrillation of duration less than the predetermined time period who receive an initial electric shock as therapy; the estimate being input into the system by the user; a user determined estimate of survival for patients with ventricular fibrillation of duration less than the predetermined time period who receive an initial therapy other than electric shock, such as cardiopulmonary resuscitation for approximately 3 minutes; the estimate being input into the system byte user; a user determined estimate of survival for patients with ventricular fibrillation of duration more than the predetermined time period who receive an initial electric shock as therapy; the estimate being input into the system by the user; the user determined estimate of survival for patients with ventricular fibrillation duration of more than the predetermined time period who receive an initial therapy other than an electric shock, such as cardiopulmonary resuscitation for approximately 3 minutes; the estimate being input into the system by the user; determining a third value which is the cutpoint or threshold that will provide maximum survival benefit based upon the survival benefit model incorporating the survival estimates input by the user as described; the step of determining the state of fibrillation relating at least one value of the first value and the second value and the third value to the state of fibrillation.

4. The method of claim 3 wherein the detennined state of ventricular fibrillation is associated with a probability of success of a mode of treatment of ventricular fibrillation, and wherein the predetermined time period is approximately 5 minutes.

5. The method of claim 4 wherein the mode of treatment is defibrillation shock.

6. The method of claim 5 wherein the probability of success of the defibrillation shook is associated with the life ratio and the logarithm of the absolute correlation.

7. A method of determining a treatment for a patient experiencing ventricular fibrillation, comprising: measuring the rhythm of the heart during ventricular fibrillation for a period of time; performing calculations to produce the discrete fourier transform from the series of voltage values that make up the measured heart rhythm; summing the power at each frequency for two frequency bands, a low frequency band and a high frequency band; determining a first value related to the high and low frequency bands by taking a quotient of the high frequency power band summation and the low frequency power band summation; and relating the first value to a treatment for the patient.

8. The method of claim 7 further comprising:
determining a second value related to a logarithm of the absolute correlation of the ventricular fibrillation heart rhythm for the period of time, the step of determining the treatment including the step of relating at least one of the first value and the second value to the treatment.

9. The method of claim 8 further comprising:
a user determined estimate of the percentage of cases for which ventricular fibrillation duration is less than a predetermined time period for the particular user group; the estimate being input into the system by the user; a user determined estimate of survival for patients with ventricular fibrillation of duration less than the predetermined time period who receive an initial electric shock as therapy; the estimate being input into the system by the user; a user determined estimate of survival for patients with ventricular fibrillation of duration less than the predetermined time period who receive an initial therapy other than electric shock, such as cardiopulmonary resuscitation for approximately 3 minutes; the estimate being input into the system byte user; a user determined estimate of survival for patients with ventricular fibrillation of duration more than the predetermined time period who receive an initial electric shock as therapy; the estimate being input into the system by the user; the user determined estimate of survival for patients with ventricular fibrillation duration of more than the predetermined time period who receive an initial therapy other than an electric shock, such as cardiopulmonary resuscitation for approximately 3 minutes; the estimate being input into the system by the user; determining a third value which is the cutpoint or threshold that will provide maximum survival benefit based upon the survival benefit model incorporating the survival estimates input by the user as described; the step of determining the treatment including the step of relating at least one of the first value and the second value and the third value to the treatment.

10. The method of claim 9 wherein the determination of the treatment comprises relating at least one of the first value and the second value and the third value to a probability of success of defibrillation shock, and wherein the predetermined time period is approximately 5 minutes.

11. A system for providing an indication of a state of ventricular fibrillation, comprising: at least one sensor to measure heart rhythm; at least one processor in communication with the sensor, to processor being configured to perform calculations to produce the discrete fourier transform from to series of voltage values that make up the measured heart rhythm; summing the power at each frequency for two frequency bands, a low frequency band and a high frequency band; determining a first value related to the high and low frequency bands by taking to quotient of the high frequency power band summation and the low frequency power band summation; and a user interface system in operative connection with the processor, the user interface system configured to provide information related to the first value.

12. The system of claim 11 wherein the processor is further configured to determine a second value related to a logarithm of the absolute correlation of the ventricular fibrillation heart rhythm for the period of time, the user interface system configured to provide information related to at least one of the first value and second value.

13. The system of claim 12 further comprising:
a user detennined estimate of to percentage of cases for which ventricular fibrillation duration is less than a predetermined time period for the particular user group; to estimate being input into the system by the user; a user determined estimate of survival for patients with ventricular fibrillation of duration less than the predetermined time period who receive an initial electric shock as therapy; the estimate being input into the system by the user; a user determined estimate of survival for patients with ventricular fibrillation of duration less than the predetermined time period who receive an initial therapy other than electric shock, such as cardiopulmonary resuscitation for approximately 3 minutes; the estimate being input into the system by the user; a user determined estimate of survival for patients with ventricular fibrillation of duration more than the predetermined time period who receive an initial electric shock as therapy; the estimate being input into the system by the user; the user determined estimate of survival for patients with ventricular fibrillation duration of more than the predetermined time period who receive an initial therapy other than an electric shock, such as cardiopulmonary resuscitation for approximately 3 minutes; the estimate being input into the system by the user; the processor being configured to determine a third value which is the cutpoint or threshold that will provide maximum survival benefit based upon the survival benefit model incorporating the survival estimates input by the user as described, the user interface system configured to provide information related to at least one of the first value and the second value and the third value.

14. The system of claim 13 wherein the user interface provides an indication of the probability of success of at least one method of treatment as a function of time, and wherein the predetermined time period is approximately 5 minutes.

15. The system of claim 14 wherein the treatment is a defibrillation shock.

16. A defibrillation system for use in treatment of ventricular fibrillation, comprising: at least one sensor to measure heart rhythm; at least one applicator to apply a defibrillation pulse to a patient; and at least one processor in communication with the sensor and the applicator, the processor being configured to perform calculations to produce a discrete fourier transform from the series of voltage values that make up the measured heart rhythm; summing the power at each frequency for two frequency bands, a low frequency band and a high frequency band; determining a first value related to the high and low frequency bands by taking the quotient of the high frequency power band summation and the low frequency power band summation over the period of time; and a user interface system in operative connection with the processor, the user interface system configured to provide information related to the first value.

17. The system of claim 16 wherein the processor is further configured to determine a second value related to a logarithm of the absolute correlation of the ventricular fibrillation heart rhythm for the period of time, the user interface providing information related to at least one of the first value and the second value.

18. The system of claim 17 further comprising:
a user determined estimate of the percentage of cases for which ventricular fibrillation duration is less than a predetermined time period for the particular user group; the estimate being input into the system by the user; a user determined estimate of survival for patients with ventricular fibrillation of duration less than the predetermined time period who receive an electric shock as initial therapy; the estimate being input into the system by the user; a user determined estimate of survival for patients with ventricular fibrillation of duration less than the predetermined time period who receive an initial therapy other than electric shock, such as cardiopulmonary resuscitation for approximately 3 minutes; the estimate being input into the system by the user; a user determined estimate of survival for patients with ventricular fibrillation of duration more than the predetermined time period who receive an initial electric shock as therapy; the estimate being input into the system by the user; the user determined estimate of survival for patients with ventricular fibrillation duration of more than the predetermined time period who receive an initial therapy other than an electric shock, such as cardiopulmonary resuscitation for approximately 3 minutes; the estimate being input into the system by the user; the processor being configured to determine a third value which is the cutpoint or threshold that will provide maximum survival benefit based upon the survival benefit model incorporating the survival estimates input by the user as described, the user interface system configured to provide information related to at least one of the first value and the second value and the third value.

19. The system of claim 18 wherein the user interface provides an indication of the probability of success of a defibrillation shock, and wherein the predetermined time period is approximately 5 minutes.

20. A method of creating a relation to characterize ventricular fibrillation, comprising: measuring the heart rhythm during ventricular fibrillation for an epoch comprising a period of time for a number of unique epochs; performing calculations to produce a discrete fourier transform from the series of voltage values that make up the measured heart rhythm; summing the power at each frequency for two frequency bands, a low frequency band and a high frequency band; taking a quotient of the high frequency power band summation and the low frequency power band summation for each epoch and determining a first value related to the quotient for each epoch.

21. The method of claim 20 wherein the unique epochs are sequential epochs.

22. The method of claim 21 wherein the unique epochs are sequential 5-second epochs.

23. A method of determining a state of a heart rhythm waveform, comprising: measuring the rhythm of the heart for a period of time; performing calculations to produce a discrete fourier transform from the series of voltage values that make up the measured heart rhythm; summing the power at each frequency for two frequency bands, a low frequency band and a high frequency band; determining a first value related to the high and low frequency bands by taking the quotient of the high frequency power band summation and the low frequency power band summation over the period of time; and determining the state of the heart rhythm waveform by relating the first value to the state of the heart rhythm waveform.

* * * * *